(12) United States Patent
Wahba

(10) Patent No.: US 10,233,486 B2
(45) Date of Patent: Mar. 19, 2019

(54) METHOD FOR INLINE BILAYER CAPACITANCE MONITORING

(71) Applicant: Roche Sequencing Solutions, Inc., Pleasanton, CA (US)

(72) Inventor: Ashraf Wahba, Hayward, CA (US)

(73) Assignee: Roche Sequencing Solutions, Inc., Pleasanton, CA (US)

( * ) Notice: Subject to any disclaimer, the term of this patent is extended or adjusted under 35 U.S.C. 154(b) by 0 days.

(21) Appl. No.: 15/715,669

(22) Filed: Sep. 26, 2017

(65) Prior Publication Data

US 2018/0080919 A1 Mar. 22, 2018

Related U.S. Application Data

(63) Continuation-in-part of application No. 15/085,700, filed on Mar. 30, 2016.

(51) Int. Cl.
| | |
|---|---|
| *G01N 27/416* | (2006.01) |
| *C12Q 1/68* | (2018.01) |
| *G01R 27/26* | (2006.01) |
| *C12Q 1/6869* | (2018.01) |
| *G01N 33/487* | (2006.01) |

(52) U.S. Cl.
CPC ............. *C12Q 1/68* (2013.01); *C12Q 1/6869* (2013.01); *G01N 33/48721* (2013.01); *G01R 27/26* (2013.01)

(58) Field of Classification Search
CPC ................................................ G01N 33/48721
See application file for complete search history.

(56) References Cited

U.S. PATENT DOCUMENTS

| | | | |
|---|---|---|---|
| 9,678,055 B2 * | 6/2017 | Chen | ................ G01N 33/48721 |
| 2014/0034497 A1 | 2/2014 | Randall | |
| 2015/0275287 A1 | 10/2015 | Tian | |

FOREIGN PATENT DOCUMENTS

| | | |
|---|---|---|
| WO | 2009024775 | 2/2009 |
| WO | 2011097028 | 8/2011 |
| WO | 2013188841 | 12/2013 |

(Continued)

OTHER PUBLICATIONS

Goldstein et al., "CMOS Low Current Measurement System for Biomedical Applications," IEEE Transactions on Biomedical Circuits and Systems, vol. 6, No. 2, Apr. 2012 (Year: 2012).*

(Continued)

*Primary Examiner* — Alexander S Noguerola
(74) *Attorney, Agent, or Firm* — Van Pelt, Yi & James LLP

(57) ABSTRACT

A method of detecting a state of a lipid membrane in a cell of a nanopore based sequencing chip is disclosed. A lipid membrane is coupled with an integrating capacitor, wherein the lipid membrane is between a working electrode and a counter electrode. An alternating current (AC) voltage is applied to the counter electrode. A voltage across the integrating capacitor is periodically sampled by an analog-to-digital converter (ADC). A change in the sampled voltage across the integrating capacitor in response to an intermediate change in the AC voltage is determined. A state of the lipid membrane is determined based on the determined change in the sampled voltage across the integrating capacitor in response to the intermediate change in the AC voltage.

18 Claims, 25 Drawing Sheets

(56) References Cited

FOREIGN PATENT DOCUMENTS

WO 2015061510 4/2015

OTHER PUBLICATIONS

Novák et al., "BLM Analyzer: a software tool for experiments on planar bilayers," Biotechniques vol. 42, No. 3, 2007, pp. 335-341 (Year: 2007).*

Dissertation entitled "Bilayer Lipid Membrane (BLM) Integration into Microfluidic Platforms with Application Toward BLM-Based Biosensors," by Louis Hromada, Jr. Graduate School of the University of Maryland, College Park, 2007 (Year: 2007).*

Polak et al., "System for Measuring Planar Lipid Bilayer Properties," J. Membrane Biol. (2012) 245:025-032 (Year: 2012).*

Article by the Krantz Lab at the University of California, Berkeley, entitled, "Planar lipid electrophysiology", last updated Oct. 6, 2007, downloaded Mar. 27, 2018 from http://mcb.berkeley.edu/labs/krantz/equipment/blm.html (Year: 2007).*

Gross et al., Determining Membrane Capacitance by Dynamic Control of Droplet Interface Bilayer Area, Langmuir, 2011, 27, pp. 14335-14342.

Osaki et al., Multichannel Simultaneous Measurements of Single-Molecule Translocation in a-Hemolysin Nanopore Array, American Chemical Society, Nov. 12, 2009.

Sandison et al., Air-Exposure Technique for the Formation of Artificial Lipid Bilayers in Microsystems, Langmuir 2007, 23, p. 8277-8284.

Suzuki et al., Highly Reproducible Method of Planar Lipid Bilayer Reconstitution in Polymethyl Methacrylate Microfluidic Chip, Langmuir 2006, 22, pp. 1937-1942.

Zagnoni, Controlled Delivery of Proteins in Bilayer Lipid Membranes on Chip, Jun. 27, 2007.

* cited by examiner

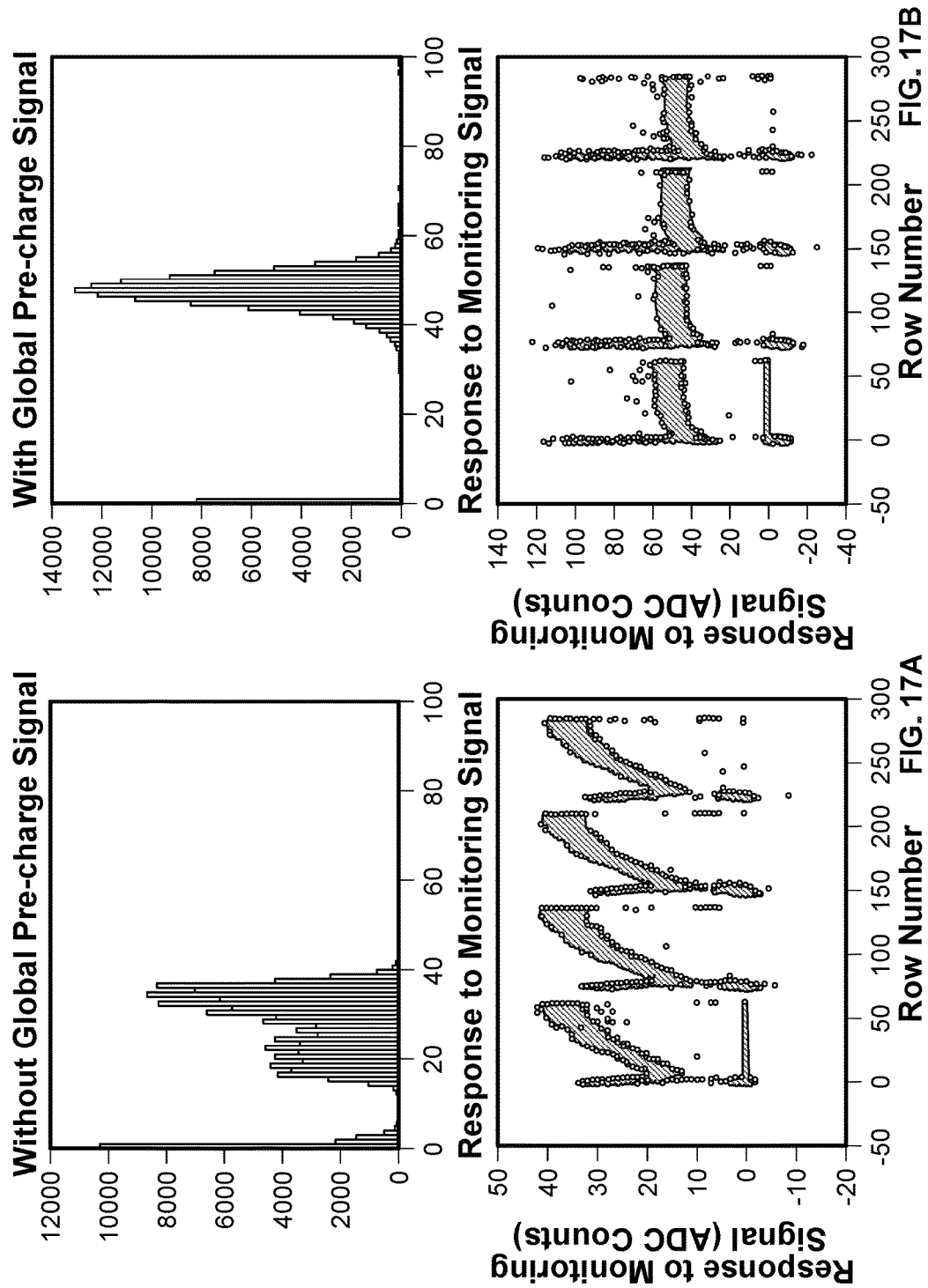

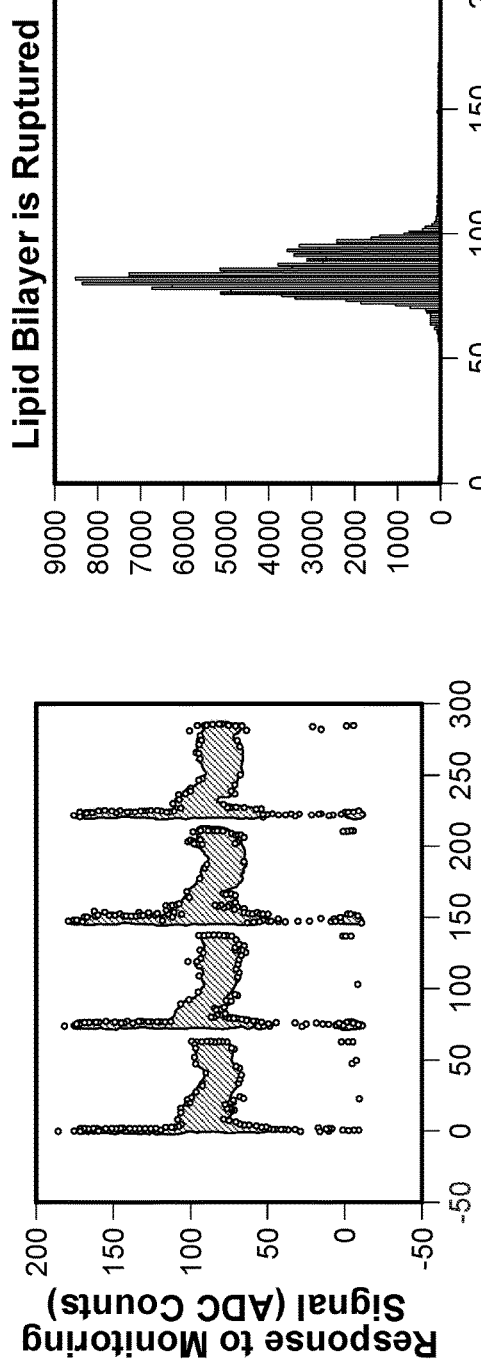
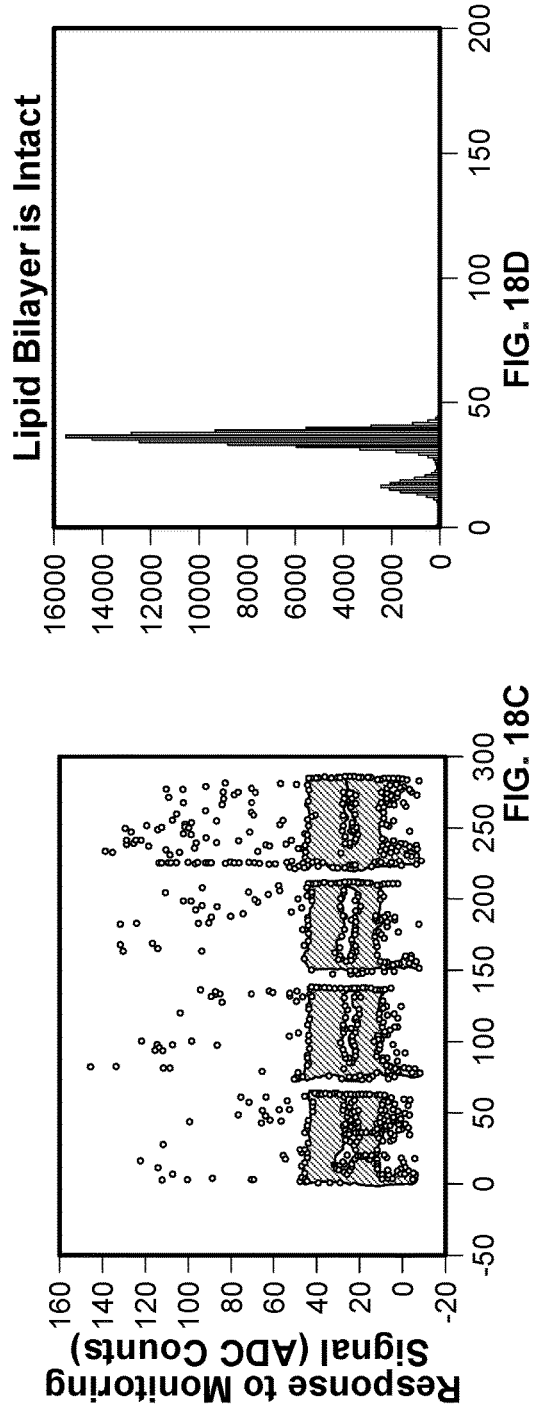
FIG. 18A  FIG. 18B  FIG. 18C  FIG. 18D

METHOD FOR INLINE BILAYER CAPACITANCE MONITORING

CROSS REFERENCE TO OTHER APPLICATIONS

This application is a continuation in part of co-pending U.S. patent application Ser. No. 15/085,700 entitled NON-DESTRUCTIVE BILAYER MONITORING USING MEASUREMENT OF BILAYER RESPONSE TO ELECTRICAL STIMULUS filed Mar. 30, 2016 which is incorporated herein by reference for all purposes.

BACKGROUND OF THE INVENTION

Advances in micro-miniaturization within the semiconductor industry in recent years have enabled biotechnologists to begin packing traditionally bulky sensing tools into smaller and smaller form factors, onto so-called biochips. Biochips may be used for nanopore-based sequencing.

The step of inserting a nanopore into a lipid bilayer is performed after it is determined that a lipid bilayer has been properly formed within a cell of the nanopore based sequencing chip. In some techniques, the process of determining whether a lipid bilayer has been properly formed in a cell may cause an already properly formed lipid bilayer to be destroyed. In other words, the stimulus voltage for testing the lipid bilayer may be destructive to the lipid bilayer. In the event that an already properly formed lipid bilayer is destroyed by the stimulus voltage, a very high current begins to flow across the electrodes as a result of the short-circuit condition. In response, the system may try to re-form a new lipid bilayer in the particular cell again; however, this is both time-consuming and inefficient. In addition, the lipid bilayer may not re-form in the particular cell in a subsequent trial. As a result, the overall percentage of cells in the nanopore based sequencing chip with properly formed lipid bilayers and nanopores (i.e., the yield of the nanopore based sequencing chip) is reduced. It would be desirable to develop techniques for nanopore-based sequencing biochips that make them more robust, efficient, and cost-effective.

SUMMARY OF THE INVENTION

In one aspect, the present invention provides methods of detecting a state of a lipid membrane in a cell of a nanopore based sequencing chip. In one embodiment, the method comprises the step of coupling a lipid membrane with an integrating capacitor. In an additional embodiment, the lipid membrane is disposed between a working electrode and a counter electrode. In another embodiment, the method further comprises the step of applying an alternating current (AC) voltage to the counter electrode. In one other embodiment, the method further comprises the step of periodically sampling a voltage across the integrating capacitor by an analog-to-digital converter (ADC). In another embodiment, the method further comprises the step of determining a change in the sampled voltage across the integrating capacitor. In one additional embodiment, the determined change is in response to an intermediate change in the AC voltage. In one embodiment, the method further comprises the step of detecting a state of the lipid membrane based on the determined change in the sampled voltage across the integrating capacitor. In one additional embodiment, the determined change is in response to the intermediate change in the AC voltage. In other embodiments, the step of determining a change in the sampled voltage across the integrating capacitor in response to the intermediate change in the AC voltage further comprises inserting the intermediate change in the AC voltage between two magnitudes of the AC voltage. In one other embodiment, the method further comprises, in response to the detection that the lipid bilayer has ruptured, the step of disabling further electrical stimuli from being applied across the lipid bilayer by opening a switch in the cell.

In one other embodiment, the method further comprises determining the change in the sampled voltage across the integrating capacitor in response to the intermediate change in the AC voltage. In one embodiment, the determining step is performed (i) when the AC voltage is switching from a first phase to a second phase; or (ii) when the AC voltage is switching from the second phase to the first phase. In one further embodiment, the AC voltage first phase comprises a first phase magnitude and the AC voltage second phase comprises a second phase magnitude. In one additional embodiment, the first phase magnitude of the AC voltage is greater than the second phase magnitude of the AC voltage. In another embodiment, the first phase comprises a positive square wave and the second phase comprises a negative square wave. In one other embodiment, the AC voltage is at an intermediate monitoring magnitude, wherein the intermediate monitoring magnitude is smaller than the first phase magnitude but greater than the second phase magnitude. In one additional embodiment, the method further comprises the step of selecting the intermediate monitoring magnitude based at least in part on an ADC reference window of the ADC.

In one embodiment, the method further comprises the step of comparing the change in the sampled voltage across the integrating capacitor against one or more predetermined thresholds. In another embodiment, the method further comprises the step of detecting the state of the lipid membrane based on the comparisons against the one or more predetermined thresholds. In one other embodiment, the state of the lipid membrane is selected from the group consisting of: a lipid membrane with more than two lipid molecule layers, a lipid bilayer, and a ruptured lipid bilayer. In a further embodiment, the method further comprises the step of selecting the intermediate monitoring magnitude such that the sampled voltage across the integrating capacitor is within an ADC reference window of the ADC in the event that the lipid bilayer has ruptured.

In one other aspect, the present invention provides methods that comprise determining the change in the sampled voltage across the integrating capacitor in response to the intermediate change in the AC voltage, wherein the cell is one of a plurality of cells in a nanopore-based sequencing chip. In one embodiment, the determining step is performed (i) when the AC voltage is switching from a first phase to a second phase; or (ii) when the AC voltage is switching from the second phase to the first phase. In one further embodiment, the AC voltage first phase comprises a first phase magnitude and the AC voltage second phase comprises a second phase magnitude. In one additional embodiment, the first phase magnitude of the AC voltage is greater than the second phase magnitude of the AC voltage. In one other embodiment, the method further comprises the step of pre-charging the integrating capacitor by connecting the integrating capacitor to a constant pre-charging voltage source using a global pre-charge signal. In another embodiment, the global pre-charge signal is used to control a timing of the pre-charging of integrating capacitors in the plurality of cells. In one additional embodiment, the method further comprises, after the integrating capacitor is charged to the constant pre-charging voltage source value, the step of disconnecting the pre-charging voltage source from the integrating capacitor using the global pre-charge signal. In one other embodiment the global pre-charge signal is used to control a timing of the disconnecting of the pre-charging voltage source from integrating capacitors in the plurality of cells. In a further embodiment, the method further comprises the step of waiting a predetermined period of time for the integrating capacitor to charge or discharge through a capacitance associated with the lipid bilayer. In one other embodiment, the method further comprises the step of sampling the voltage across the integrating capacitor after the predetermined waiting period. In one embodiment, the timing of the disconnecting of the pre-charging voltage source from integrating capacitors in the plurality of cells is configured such that the timing is substantially the same as a timing when the AC voltage is switched to the intermediate monitoring magnitude. In another embodiment, the timing of the pre-charging of integrating capacitors in the plurality of cells is configured such that the timing is after a frame of sequencing data from the plurality of cells has been read out. In an additional embodiment, the frame is one frame prior to a frame when the AC voltage is switched to the intermediate monitoring magnitude.

In one additional aspect, the present invention provides a system for detecting a state of a lipid membrane in a cell of a nanopore based sequencing chip. In one embodiment, the system comprises an integrating capacitor. In another embodiment, the system further comprises a working electrode coupled to the integrating capacitor. In another embodiment, the system further comprises a counter electrode. In another embodiment, a lipid membrane is deposited (or disposed) between the working electrode and the counter electrode. In another embodiment, the lipid membrane is coupled with the integrating capacitor. In another embodiment, the system further comprises an alternating current (AC) voltage source that applies an AC voltage to the counter electrode. In another embodiment, the system further comprises an analog-to-digital converter (ADC) periodically sampling a voltage across the integrating capacitor. In another embodiment, the system further comprises a processor or a circuitry.

In another embodiment, the processor or circuitry is configured to determine a change in the sampled voltage across the integrating capacitor in response to an intermediate change in the AC voltage. In a further embodiment, the processor or circuitry is further configured to detect a state of the lipid membrane based on the determined change in the sampled voltage across the integrating capacitor in response to the intermediate change in the AC voltage. In an additional embodiment, the processor or circuitry is configured to determine a change in the sampled voltage across the integrating capacitor in response to the intermediate change in the AC voltage, wherein the determining comprises inserting the intermediate change in the AC voltage between two magnitudes of the AC voltage. In another embodiment, the processor or circuitry is further configured to determine the change in the sampled voltage across the integrating capacitor in response to the intermediate change in the AC voltage when the AC voltage is switching from a first phase to a second phase or when the AC voltage is switching from the second phase to the first phase. In one further embodiment, the AC voltage first phase comprises a first phase magnitude and the AC voltage second phase comprises a second phase magnitude. In one additional embodiment, the first phase magnitude of the AC voltage is greater than the second phase magnitude of the AC voltage. In another embodiment, the first phase comprises a positive square wave and the second phase comprises a negative square wave. In an additional embodiment, the processor or circuitry is further configured to determine the change in the sampled voltage across the integrating capacitor in response to the intermediate change in the AC voltage when the AC voltage is at an intermediate monitoring magnitude. In one other embodiment, the intermediate monitoring magnitude is smaller than the first phase magnitude but greater than the second phase magnitude. In another embodiment, the processor or circuitry is further configured to select the intermediate monitoring magnitude based at least in part on a ADC reference window of the ADC. In an additional embodiment, the processor or circuitry is further configured to compare the change in the sampled voltage across the integrating capacitor against one or more predetermined thresholds. In one embodiment, the processor or circuitry is further configured to detect the state of the lipid membrane based on the comparisons against the one or more predetermined thresholds. In one additional embodiment, the state of the lipid membrane is selected from the group consisting of: a lipid membrane with more than two lipid molecule layers, a lipid bilayer, and a ruptured lipid bilayer.

In another aspect, the present invention provides a system for detecting a state of a lipid membrane in a cell of a nanopore based sequencing chip, wherein the system comprises a processor or circuitry configured to determine the change in the sampled voltage across the integrating capacitor in response to the intermediate change in the AC voltage, wherein the cell is one of a plurality of cells in a nanopore-based sequencing chip. In one embodiment, the intermediate monitoring magnitude is smaller than the first phase magnitude but greater than the second phase magnitude. In another embodiment, the system further comprises a constant pre-charging voltage source. In one additional embodiment, the processor or circuitry is further configured to pre-charge the integrating capacitor by connecting the integrating capacitor to the constant pre-charging voltage source using a global pre-charge signal. In one embodiment, the global pre-charge signal is used to control a timing of the pre-charging of integrating capacitors in the plurality of cells. In another embodiment, the processor or circuitry is further configured, after the integrating capacitor is charged to the constant pre-charging voltage source value, to disconnect the pre-charging voltage source from the integrating capacitor using the global pre-charge signal. In a further embodiment, the global pre-charge signal is used to control a timing of the disconnecting of the pre-charging voltage source from integrating capacitors in the plurality of cells. In an additional embodiment, the processor or circuitry is further configured to wait a predetermined period of time for the integrating capacitor to charge or discharge through a capacitance associated with the lipid bilayer. In one other embodiment, the processor or circuitry is further configured to cause the ADC to sample the voltage across the integrating capacitor after the predetermined waiting period. In one additional embodiment, the timing of the disconnecting of the pre-charging voltage source from integrating capacitors in the plurality of cells is configured such that the timing is substantially the same as a timing when the AC voltage is switched to the intermediate monitoring magnitude. In one embodiment, the timing of the pre-charging of integrating capacitors in the plurality of cells is configured such that the timing is after a frame of sequencing data from the plurality of cells has been read out. In another embodiment, the frame is one frame prior to a frame when the AC voltage is switched to the intermediate monitoring magnitude.

In a further embodiment, the system further comprises a switch in the cell controlled by the processor or the circuitry. In one embodiment, the processor or circuitry is further configured, in response to the detection that the lipid bilayer has ruptured, to disable further electrical stimulus from being applied across the lipid bilayer by opening the switch in the cell.

BRIEF DESCRIPTION OF THE DRAWINGS

Various embodiments of the invention are disclosed in the following detailed description and the accompanying drawings.

FIG. 11A is identical to FIG. 8B.

FIG. 17A illustrates the row dependence effect of the ruptured lipid bilayer detection technique.

FIG. 17B illustrates that the row dependence effect is significantly reduced by using the global pre-charge signal in FIG. 16.

FIG. 18A is a plot of the observed voltage change $\Delta V_{ADC}$ in response to the monitoring signal in cells that belong to different rows of a cell bank when ruptured lipid bilayers are detected.

FIG. 18B is a histogram that shows the distribution of the response signals when ruptured lipid bilayers are detected.

FIG. 18C is a plot of the observed voltage change $\Delta V_{ADC}$ in response to the monitoring signal in cells that belong to different rows of a cell bank when ruptured lipid bilayers are not detected.

FIG. 18D is a histogram that shows the distribution of the response signals when ruptured lipid bilayers are not detected.

DETAILED DESCRIPTION

The invention can be implemented in numerous ways, including as a process; an apparatus; a system; a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Nanopore membrane devices having pore sizes on the order of one nanometer in internal diameter have shown promise in rapid nucleotide sequencing. When a voltage potential is applied across a nanopore immersed in a conducting fluid, a small ion current attributed to the conduction of ions across the nanopore can be observed. The size of the current is sensitive to the pore size.

A nanopore based sequencing chip may be used for DNA sequencing. A nanopore based sequencing chip incorporates a large number of sensor cells configured as an array. For example, an array of one million cells may include 1000 rows by 1000 columns of cells.

Figure 1:
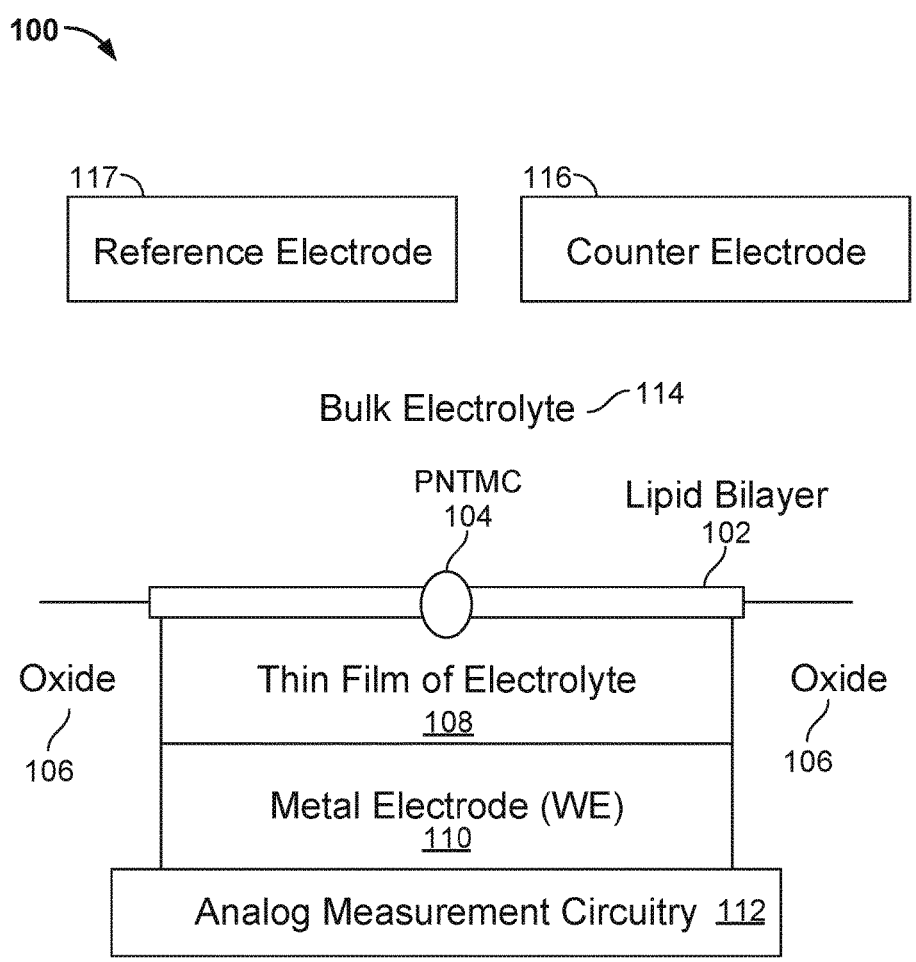
FIG. 1 illustrates an embodiment of a cell 100 in a nanopore based sequencing chip.

FIG. 1 illustrates an embodiment of a cell 100 in a nanopore based sequencing chip. A membrane 102 is formed over the surface of the cell. In some embodiments, membrane 102 is a lipid bilayer. The bulk electrolyte 114 containing soluble protein nanopore transmembrane molecular complexes (PNTMC) and the analyte of interest is placed directly onto the surface of the cell. A single PNTMC 104 is inserted into membrane 102 by electroporation. The individual membranes in the array are neither chemically nor electrically connected to each other. Thus, each cell in the array is an independent sequencing machine, producing data unique to the single polymer molecule associated with the PNTMC. PNTMC 104 operates on the analytes and modulates the ionic current through the otherwise impermeable bilayer.

With continued reference to FIG. 1, analog measurement circuitry 112 is connected to a metal electrode 110 covered by a thin film of electrolyte 108. The thin film of electrolyte 108 is isolated from the bulk electrolyte 114 by the ion-impermeable membrane 102. PNTMC 104 crosses membrane 102 and provides the only path for ionic current to flow from the bulk liquid to working electrode 110. The cell also includes a counter electrode (CE) 116, which is an electrochemical potential sensor. The cell also includes a reference electrode 117.

Figure 2:
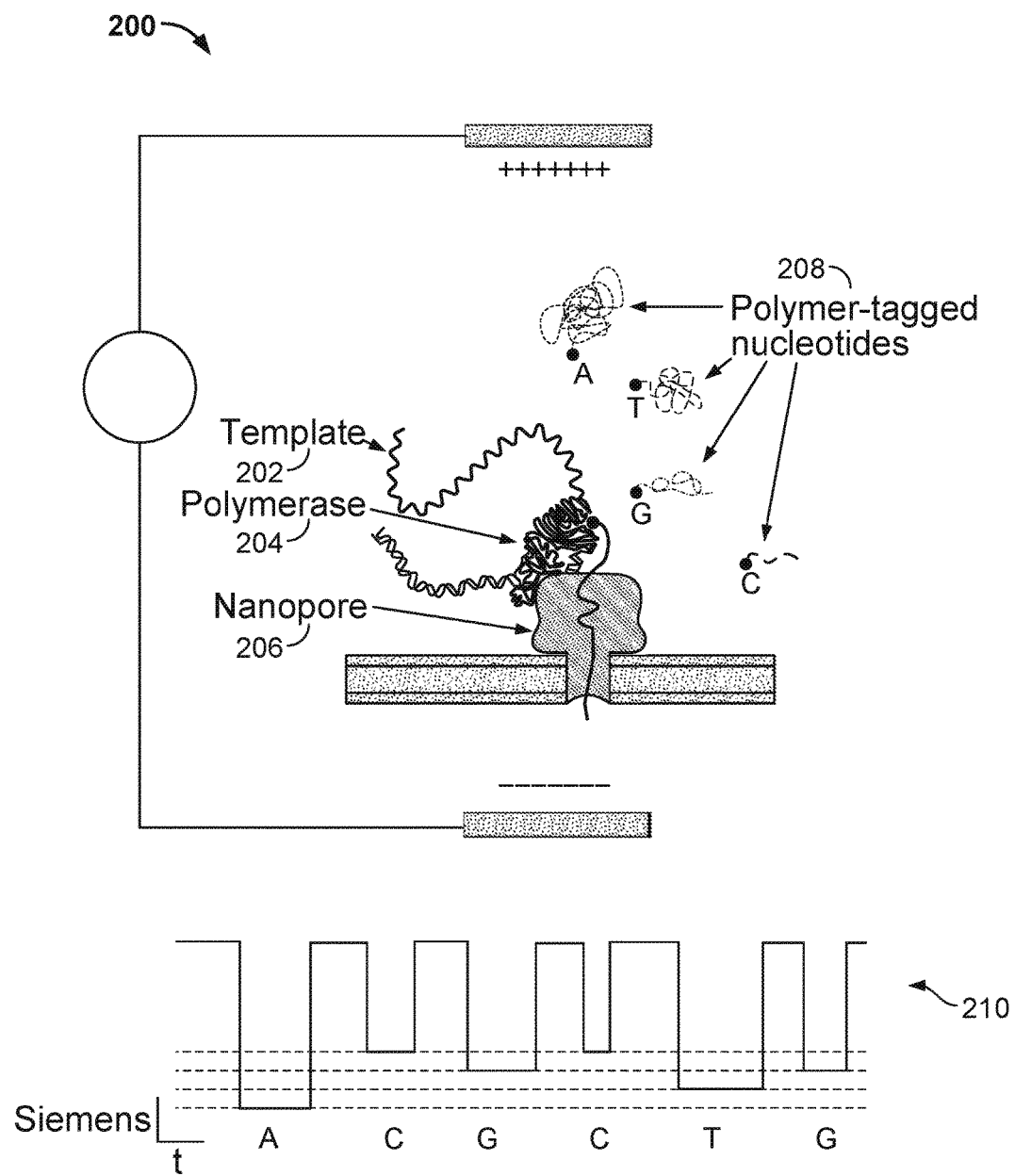
FIG. 2 illustrates an embodiment of a cell 200 performing nucleotide sequencing with the Nano-SBS technique.

In some embodiments, a nanopore array enables parallel sequencing using the single molecule nanopore-based sequencing by synthesis (Nano-SBS) technique. FIG. 2 illustrates an embodiment of a cell 200 performing nucleotide sequencing with the Nano-SBS technique. In the Nano-SBS technique, a template 202 to be sequenced and a primer are introduced to cell 200. To this template-primer complex, four differently tagged nucleotides 208 are added to the bulk aqueous phase. As the correctly tagged nucleotide is complexed with the polymerase 204, the tail of the tag is positioned in the barrel of nanopore 206. The tag held in the barrel of nanopore 206 generates a unique ionic blockade signal 210, thereby electronically identifying the added base due to the tags' distinct chemical structures.

Figure 3:
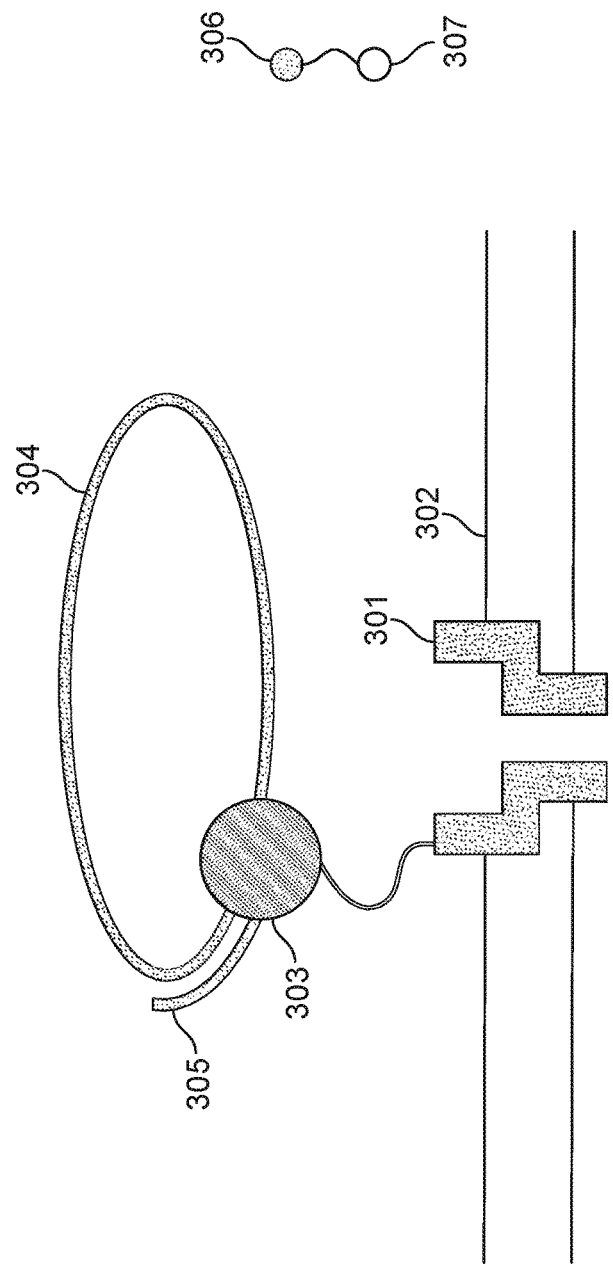
FIG. 3 illustrates an embodiment of a cell about to perform nucleotide sequencing with pre-loaded tags.

FIG. 3 illustrates an embodiment of a cell about to perform nucleotide sequencing with pre-loaded tags. A nanopore 301 is formed in a membrane 302. An enzyme 303 (e.g., a polymerase, such as a DNA polymerase) is associated with the nanopore. In some cases, polymerase 303 is covalently attached to nanopore 301. Polymerase 303 is associated with a nucleic acid molecule 304 to be sequenced. In some embodiments, the nucleic acid molecule 304 is circular. In some cases, nucleic acid molecule 304 is linear. In some embodiments, a nucleic acid primer 305 is hybridized to a portion of nucleic acid molecule 304. Polymerase 303 catalyzes the incorporation of nucleotides 306 onto primer 305 using single stranded nucleic acid molecule 304 as a template. Nucleotides 306 comprise tag species ("tags") 307.

Figure 4:
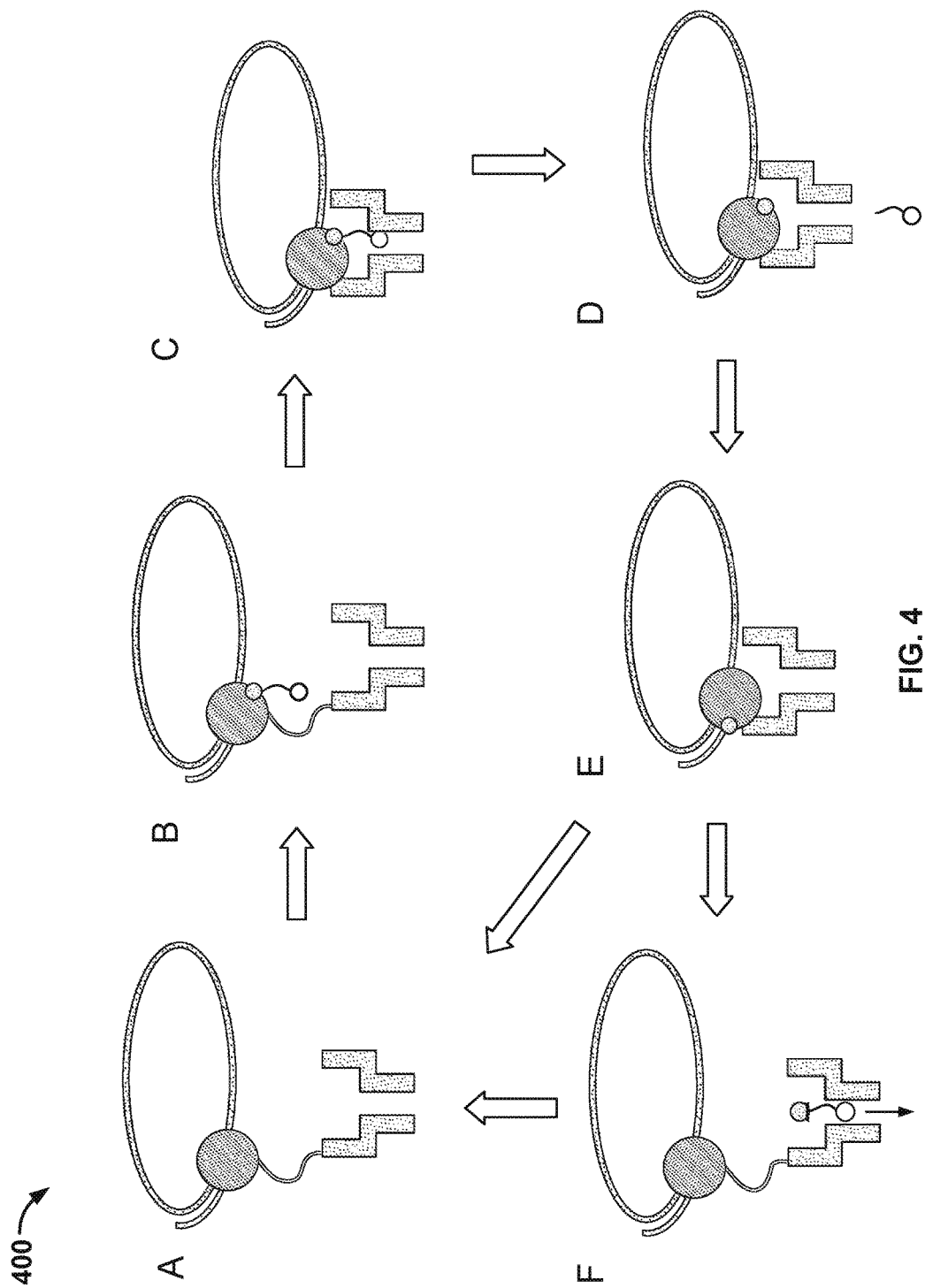
FIG. 4 illustrates an embodiment of a process 400 for nucleic acid sequencing with pre-loaded tags.

FIG. 4 illustrates an embodiment of a process 400 for nucleic acid sequencing with pre-loaded tags. Stage A illustrates the components as described in FIG. 3. Stage C shows the tag loaded into the nanopore. A "loaded" tag may be one that is positioned in and/or remains in or near the nanopore for an appreciable amount of time, e.g., 0.1 millisecond (ms) to 10000 ms. In some cases, a tag that is pre-loaded is loaded in the nanopore prior to being released from the nucleotide. In some instances, a tag is pre-loaded if the probability of the tag passing through (and/or being detected by) the nanopore after being released upon a nucleotide incorporation event is suitably high, e.g., 90% to 99%.

At stage A, a tagged nucleotide (one of four different types: A, T, G, or C) is not associated with the polymerase. At stage B, a tagged nucleotide is associated with the polymerase. At stage C, the polymerase is docked to the nanopore. The tag is pulled into the nanopore during docking by an electrical force, such as a force generated in the presence of an electric field generated by a voltage applied across the membrane and/or the nanopore.

Some of the associated tagged nucleotides are not base paired with the nucleic acid molecule. These non-paired nucleotides typically are rejected by the polymerase within a time scale that is shorter than the time scale for which correctly paired nucleotides remain associated with the polymerase. Since the non-paired nucleotides are only transiently associated with the polymerase, process 400 as shown in FIG. 4 typically does not proceed beyond stage D. For example, a non-paired nucleotide is rejected by the polymerase at stage B or shortly after the process enters stage C.

Before the polymerase is docked to the nanopore, the conductance of the nanopore is ~300 picosiemens (300 pS). At stage C, the conductance of the nanopore is about 60 pS, 80 pS, 100 pS, or 120 pS, corresponding to one of the four types of tagged nucleotides respectively. The polymerase undergoes an isomerization and a transphosphorylation reaction to incorporate the nucleotide into the growing nucleic acid molecule and release the tag molecule. In particular, as the tag is held in the nanopore, a unique conductance signal (e.g., see signal 210 in FIG. 2) is generated due to the tag's distinct chemical structures, thereby identifying the added base electronically. Repeating the cycle (i.e., stage A through E or stage A through F) allows for the sequencing of the nucleic acid molecule. At stage D, the released tag passes through the nanopore.

In some cases, tagged nucleotides that are not incorporated into the growing nucleic acid molecule will also pass through the nanopore, as seen in stage F of FIG. 4. The unincorporated nucleotide can be detected by the nanopore in some instances, but the method provides a means for distinguishing between an incorporated nucleotide and an unincorporated nucleotide based at least in part on the time for which the nucleotide is detected in the nanopore. Tags bound to unincorporated nucleotides pass through the nanopore quickly and are detected for a short period of time (e.g., less than 10 ms), while tags bound to incorporated nucleotides are loaded into the nanopore and detected for a long period of time (e.g., at least 10 ms).

Figure 5:
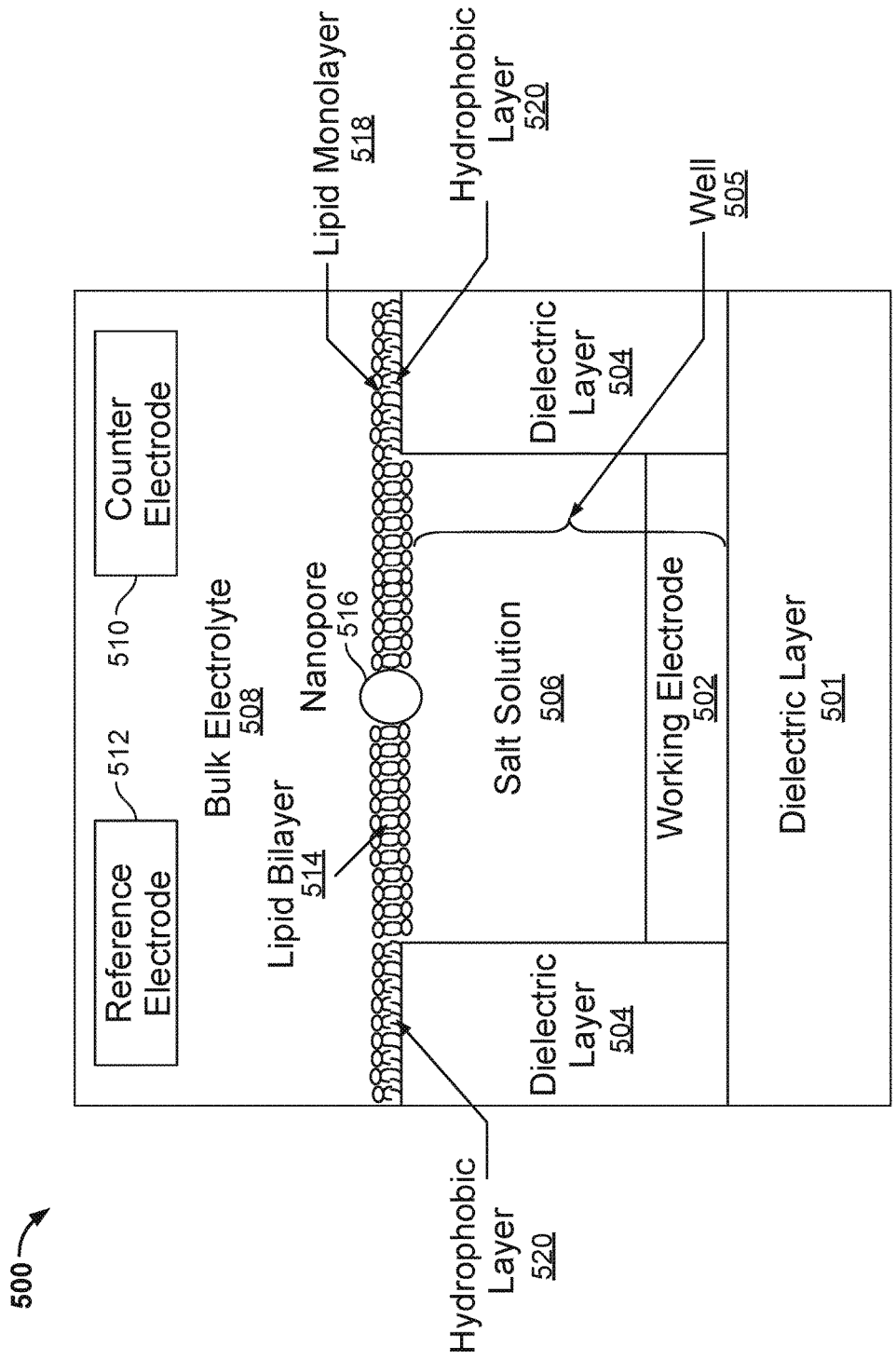
FIG. 5 illustrates an embodiment of a cell 500 in a nanopore based sequencing chip.

FIG. 5 illustrates an embodiment of a cell 500 in a nanopore based sequencing chip. Cell 500 includes a dielectric layer 501. Dielectric material used to form dielectric layer 501 includes glass, oxides, nitrides, and the like. Cell 500 further includes a dielectric layer 504 above dielectric layer 501. Dielectric layer 504 forms the walls surrounding a well 505 in which a working electrode 502 is located at the bottom. Dielectric material used to form dielectric layer 504 includes glass, oxide, silicon mononitride (SiN), and the like. The top surface of dielectric layer 504 may be silanized. Silanization forms a hydrophobic layer 520 above the top surface of dielectric layer 504. In some embodiments, hydrophobic layer 520 has a thickness of about 1.5 nanometer (nm).

Well 505 formed by the dielectric layer walls 504 further includes a film of salt solution 506 above working electrode 502. Salt solution 506 may include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$). In some embodiments, the film of salt solution 506 has a thickness of about three microns (μm).

As shown in FIG. 5, a membrane is formed on top of dielectric layer 504 and spans across well 505. For example, the membrane includes a lipid monolayer 518 formed on top of hydrophobic layer 520. As the membrane reaches the opening of well 505, the lipid monolayer transitions to a lipid bilayer 514 that spans across the opening of the well. A bulk electrolyte 508 containing protein nanopore transmembrane molecular complexes (PNTMC) and the analyte of interest is placed directly above the well. A single PNTMC/nanopore 516 is inserted into lipid bilayer 514 by electroporation. Nanopore 516 crosses lipid bilayer 514 and provides the only path for ionic flow from bulk electrolyte 508 to working electrode 502. Bulk electrolyte 508 may further include one of the following: lithium chloride (LiCl), sodium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$).

Cell 500 includes a counter electrode (CE) 510, which is an electrochemical potential sensor. Cell 500 also includes a reference electrode 512. In some embodiments, counter electrode 510 is shared between a plurality of cells, and is therefore also referred to as a common electrode. The common electrode can be configured to apply a common potential to the bulk liquid in contact with the nanopores in the measurements cells. The common potential and the common electrode are common to all of the measurement cells.

In some embodiments, working electrode 502 is a metal electrode. For non-faradaic conduction, working electrode 502 may be made of metals that are resistant to corrosion and oxidation, e.g., platinum, gold, titanium nitride and graphite. For example, working electrode 502 may be a platinum electrode with electroplated platinum. In another example, working electrode 502 may be a titanium nitride (TiN) working electrode.

The step of inserting a nanopore into a lipid bilayer is performed after it is determined that a lipid bilayer has been properly formed within a cell of the nanopore based sequencing chip. In some techniques, the process of determining whether a lipid bilayer has been properly formed in a cell may cause an already properly formed lipid bilayer to be destroyed. For example, a stimulus voltage may be applied to cause a current to flow across the electrodes. Although the measured response to the stimulus voltage may be used to distinguish between a cell with a properly formed lipid bilayer (i.e., a lipid bilayer that is two layers of lipid molecules thick) from a cell without a properly formed lipid bilayer (e.g., a cell with a thick lipid and solvent combined film that spans across the well of the cell), the stimulus voltage level is high enough to cause an already properly formed lipid bilayer to break down in some instances. In other words, the stimulus voltage for testing the lipid bilayer may be destructive to the lipid bilayer. In the event that an already properly formed lipid bilayer is destroyed by the stimulus voltage, a very high current begins to flow across the electrodes as a result of the short-circuit condition. In response, the system may try to reform a new lipid bilayer in the particular cell again; however, this is both time-consuming and inefficient. In addition, a lipid bilayer may not reform in the particular cell in a subsequent trial. As a result, the overall percentage of cells in the nanopore based sequencing chip with properly formed lipid bilayers and nanopores (i.e., the yield of the nanopore based sequencing chip) is reduced.

A non-destructive technique to detect a lipid bilayer formed in a cell of a nanopore based sequencing chip is disclosed. A non-destructive technique to detect a lipid bilayer has many advantages, including increasing the efficiency and yield of the nanopore based sequencing chip.

Figure 6A:
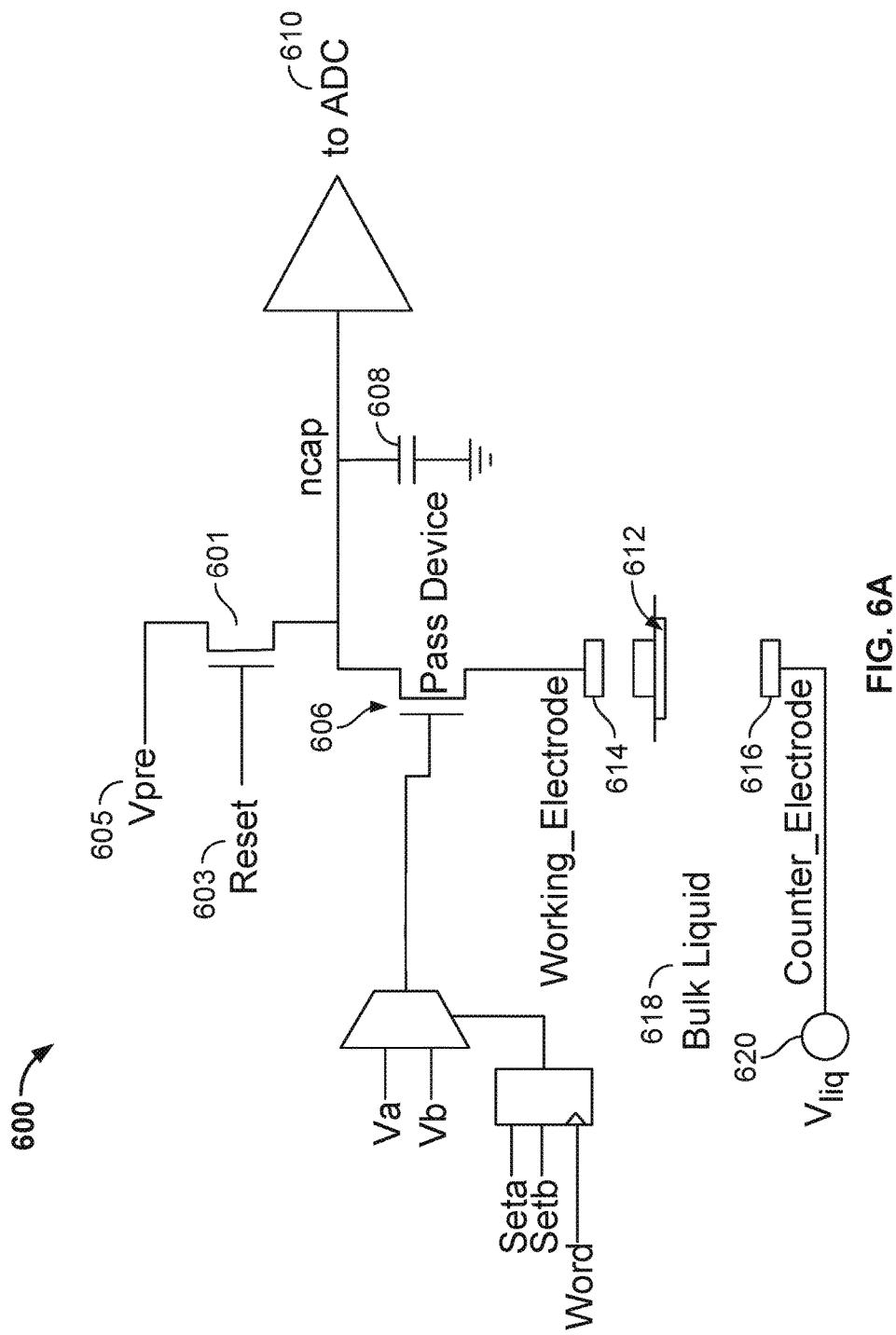
FIG. 6A illustrates an embodiment of a circuitry 600 in a cell of a nanopore based sequencing chip, wherein the circuitry can be configured to detect whether a lipid bilayer is formed in the cell without causing an already formed lipid bilayer to break down.

FIG. 6A illustrates an embodiment of a circuitry 600 in a cell of a nanopore based sequencing chip wherein the circuitry can be configured to detect whether a lipid bilayer is formed in the cell without causing an already formed lipid bilayer to break down.

FIG. 6A shows a lipid membrane or lipid bilayer 612 situated between a cell working electrode 614 and a counter electrode 616, such that a voltage is applied across lipid membrane/bilayer 612. A lipid bilayer is a thin membrane made of two layers of lipid molecules. A lipid membrane is a membrane made of several layers (more than two) of lipid molecules. Lipid membrane/bilayer 612 is also in contact with a bulk liquid/electrolyte 618. Note that working electrode 614, lipid membrane/bilayer 612, and counter electrode 616 are drawn upside down as compared to the working electrode, lipid bilayer, and counter electrode in FIG. 1. In some embodiments, the counter electrode is shared between a plurality of cells, and is therefore also referred to as a common electrode. The common electrode can be configured to apply a common potential to the bulk liquid in contact with the lipid membranes/bilayers in the measurements cells by connecting the common electrode to a voltage source $V_{liq}$ 620. The common potential and the common electrode are common to all of the measurement cells. There is a working cell electrode within each measurement cell; in contrast to the common electrode, working cell electrode 614 is configurable to apply a distinct potential that is independent from the working cell electrodes in other measurement cells.

Figure 6B:
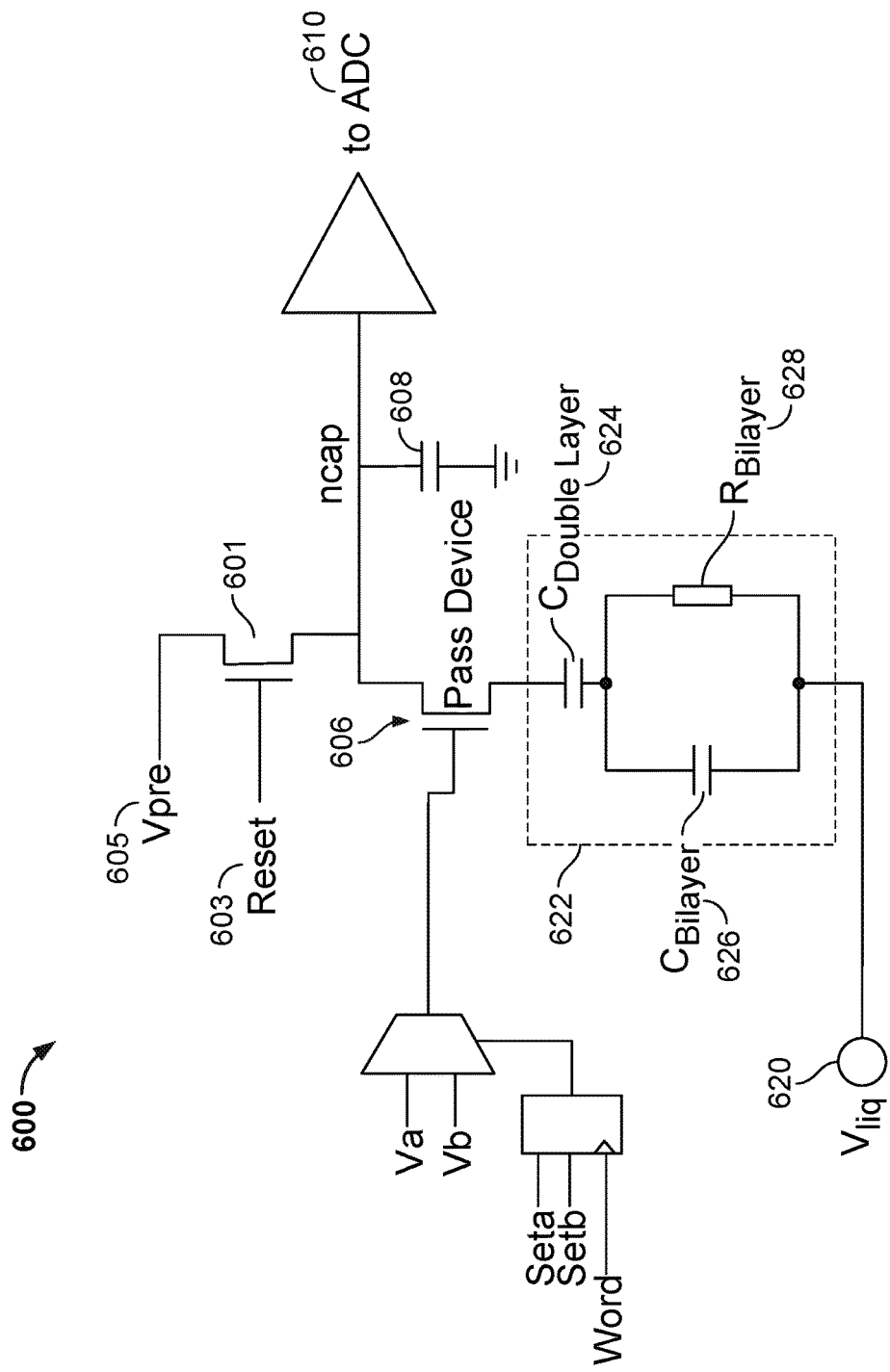
FIG. 6B illustrates the same circuitry 600 in a cell of a nanopore based sequencing chip as that shown in FIG. 6A. In comparison with FIG. 6A, instead of showing a lipid membrane/bilayer between the working electrode and the counter electrode, an electrical model representing the electrical properties of the working electrode and the lipid membrane/bilayer is shown.

FIG. 6B illustrates the same circuitry 600 in a cell of a nanopore based sequencing chip as that shown in FIG. 6A. In comparison with FIG. 6A, instead of showing a lipid membrane/bilayer between the working electrode and the counter electrode, an electrical model representing the electrical properties of the working electrode and the lipid membrane/bilayer is shown.

Electrical model 622 includes a capacitor 624 representing the electrical properties of working electrode 614. The capacitance associated with working electrode 614 is also referred to as a double layer capacitance ($C_{double\ layer}$). Electrical model 622 further includes a capacitor 626 ($C_{bilayer}$) that models a capacitance associated with the lipid membrane/bilayer and a resistor 628 ($R_{bilayer}$) that models a resistance associated with the lipid membrane/bilayer. The resistance associated with the lipid membrane/bilayer is very high, and therefore $R_{bilayer}$ may be replaced by an open circuit, which reduces electrical model 622 to $C_{double\ layer}$ in series with $C_{bilayer}$.

Voltage source $V_{liq}$ 620 is an alternating current (AC) voltage source. Counter electrode 616 is immersed in the bulk liquid 618, and an AC non-Faradaic mode is utilized to modulate a square wave voltage $V_{liq}$ and apply it to the bulk liquid in contact with the lipid membranes/bilayers in the measurement cells. In some embodiments, $V_{liq}$ is a square wave with a magnitude of ±200-250 mV and a frequency between 25 and 100 Hz.

Pass device 606 is a switch that can be used to connect or disconnect the lipid membrane/bilayer and the electrodes from the measurement circuitry 600. The switch enables or disables a voltage stimulus that can be applied across the lipid membrane/bilayer in the cell. Before lipids are deposited to the cell to form a lipid bilayer, the impedance between the two electrodes is very low because the well of the cell is not sealed, and therefore switch 606 is kept open to avoid a short-circuit condition. Switch 606 may be closed once lipid solvent has been deposited to the cell that seals the well of the cell.

Circuitry 600 further includes an on-chip fabricated integrating capacitor 608 ($n_{cap}$). Integrating capacitor 608 is pre-charged by using a reset signal 603 to close switch 601, such that integrating capacitor 608 is connected to a voltage source $V_{pre}$ 605. In some embodiments, voltage source $V_{pre}$ 605 provides a constant positive voltage with a magnitude of 900 mV. When switch 601 is closed, integrating capacitor 608 is pre-charged to the positive voltage level of voltage source $V_{pre}$ 605.

After integrating capacitor 608 is pre-charged, reset signal 603 is used to open switch 601 such that integrating capacitor 608 is disconnected from voltage source $V_{pre}$ 605. At this point, depending on the level of $V_{liq}$, the potential of counter electrode 616 may be at a higher level than the potential of working electrode 614, or vice versa. For example, during the positive phase of square wave $V_{liq}$ (i.e., the dark period of the AC voltage source signal cycle), the potential of counter electrode 616 is at a higher level than the potential of working electrode 614. Similarly, during the negative phase of square wave $V_{liq}$ (i.e., the bright period of the AC voltage source signal cycle), the potential of counter electrode 616 is at a lower level than the potential of working electrode 614. Due to this potential difference, integrating capacitor 608 may be charged during the dark period of the AC voltage source signal cycle and discharged during the bright period of the AC voltage source signal cycle.

Depending on the sampling rate of an analog-to-digital converter (ADC) 610, integrating capacitor 608 charges or discharges for a fixed period of time, and then the voltage stored in integrating capacitor 608 may be read out by ADC 610. After the sampling by ADC 610, integrating capacitor 608 is pre-charged again by using reset signal 603 to close switch 601, such that integrating capacitor 608 is connected to voltage source $V_{pre}$ 605 again. In some embodiments, the sampling rate of ADC 610 is between 1500 to 2000 Hz. In some embodiments, the sampling rate of ADC 610 is up to 5 kHz. For example, with a sampling rate of 1 kHz, integrating capacitor 608 charges or discharges for a period of ~1 ms, and then the voltage stored in integrating capacitor 608 is read out by ADC 610. After the sampling by ADC 610, integrating capacitor 608 is pre-charged again by using reset signal 603 to close switch 601 such that integrating capacitor 608 is connected to voltage source $V_{pre}$ 605 again. The steps of pre-charging the integrating capacitor 608, waiting a fixed period of time for the integrating capacitor 608 to charge or discharge, and sampling the voltage stored in integrating capacitor by ADC 610 are then repeated in cycles throughout a lipid bilayer measurement phase of the system.

Circuitry 600 may be used to detect whether a lipid bilayer is formed in the cell by monitoring a delta voltage change, $\Delta V_{ADC}$, at integrating capacitor 608 ($n_{cap}$) in response to a delta voltage change ($\Delta V_{liq}$) applied to the bulk liquid in contact with the lipid membrane/bilayer. As will be described in greater detail below, during the lipid bilayer measurement phase, circuitry 600 may be modeled as a voltage divider with $C_{bilayer}$ 626, $C_{double\ layer}$ 624, and $n_{cap}$ 608 connected in series, and a voltage change tapped at an intermediate point of the voltage divider can be read by ADC 610 for determining whether a lipid bilayer has been formed.

Figure 7:
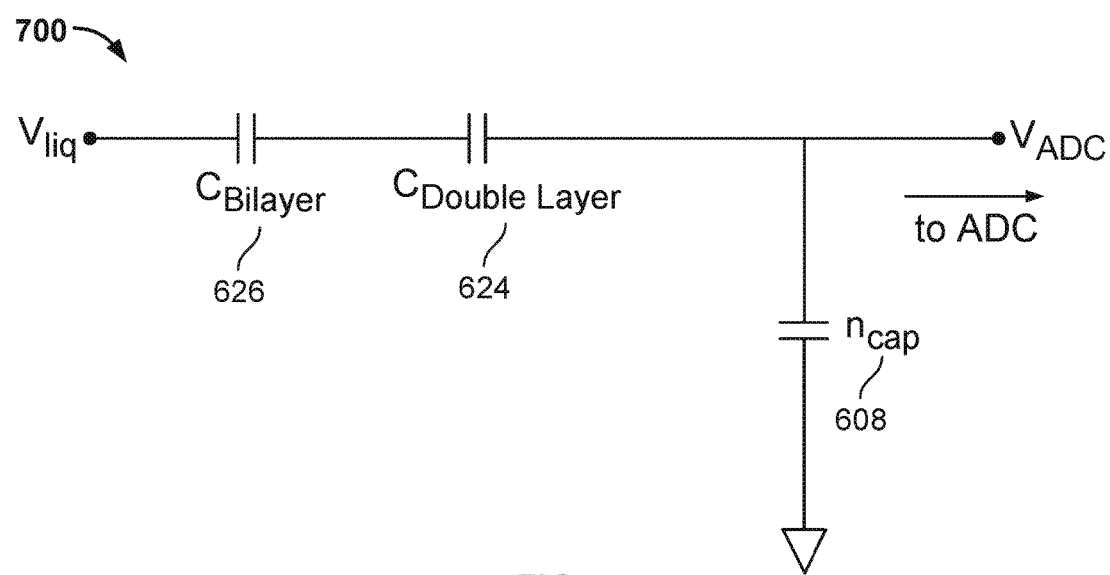
FIG. 7 illustrates an electrical model 700 representing the electrical properties of a portion of circuitry 600 during the lipid bilayer measurement phase of the system.

FIG. 7 illustrates an electrical model 700 representing the electrical properties of a portion of circuitry 600 during the lipid bilayer measurement phase of the system. As shown in FIG. 7, $C_{double\ layer}$ 624 is connected in series with $C_{bilayer}$ 626, but $R_{bilayer}$ 628 (see FIG. 6B) is eliminated from electrical model 700. $R_{bilayer}$ 628 can be removed from electrical model 700 because the resistance associated with the lipid membrane/bilayer is very high, and therefore $R_{bilayer}$ may be approximated as an open circuit. As shown in FIG. 7, $C_{double\ layer}$ 624 and $C_{bilayer}$ 626 are further connected in series with $n_{cap}$ 608.

When operating in an AC mode, the voltage read by the ADC ($V_{ADC}$) can be determined by:

$$V_{ADC} = V_{liq} * \frac{Z(ncap)}{Z(\text{bilayer}) + Z(\text{double layer}) + Z(ncap)} \quad \text{Equation (1)}$$

where $Z = 1/(j\omega C)$,

Z(ncap) is the AC impedance associated with $n_{cap}$,

Z(double layer) is the AC impedance associated with the working electrode, and Z(bilayer) is the AC impedance associated with the lipid membrane/bilayer.

The AC impedance of the double layer, Z(double layer), has a very low value compared to Z(bilayer) and Z(ncap) because $C_{double\ layer}$ is much larger than $C_{bilayer}$ or the capacitance of $n_{cap}$. Therefore, substituting Z(ncap)=1/($j\omega C_{ncap}$), Z(bilayer)=1/$j\omega C_{bilayer}$, and Z(double layer)=0, equation (1) can be simplified as:

$$V_{ADC} = V_{liq} * \frac{C(\text{bilayer})}{C(\text{ncap}) + C(\text{bilayer})} \quad \text{Equation (2)}$$

where C(ncap) is the capacitance associated with $n_{cap}$, and C(bilayer) is the capacitance associated with the lipid membrane/bilayer.

When lipids are first deposited into the cells to form the lipid bilayers, some of the cells have lipid bilayers spontaneously formed, but some of the cells merely have a thick lipid membrane (with multiple layers of lipid molecules and solvent combined together) spanning across each of the wells of the cells. The capacitance associated with a lipid bilayer is larger than the capacitance associated with a lipid membrane that is more than two layers of lipid molecules thick because the capacitance of the lipid membrane/bilayer is inversely proportional to its thickness. As a lipid membrane thins out and transitions to become a lipid bilayer, the thickness decreases and its associated capacitance increases. In Equation (2) above, as a lipid bilayer begins to form within a cell, C(bilayer) increases while C(ncap) remains constant, such that on the whole $V_{ADC}$ increases. An increase in $V_{ADC}$ can therefore be used as an indicator that a lipid bilayer has been formed within a cell.

In some embodiments, a delta voltage change $\Delta V_{ADC}$ at integrating capacitor 608 ($n_{cap}$) in response to a delta voltage change ($\Delta V_{liq}$) applied to the bulk liquid in contact with the lipid membrane/bilayer is monitored in order to detect whether a lipid bilayer has been formed in a cell. For example, Equation (2) may be rewritten as:

$$\Delta V_{ADC} = \Delta V_{liq} * \frac{C(\text{bilayer})}{C(\text{ncap}) + C(\text{bilayer})} \quad \text{Equation (3)}$$

where $\Delta V_{ADC}$ is a voltage change at integrating capacitor 608 ($n_{cap}$) read by the ADC,
$\Delta V_{liq}$ is a voltage change applied to the bulk liquid,
C(ncap) is the capacitance associated with $n_{cap}$,
and C(bilayer) is the capacitance associated with the lipid membrane/bilayer.

In Equation (3) above, because C(ncap) remains constant, while C(bilayer) increases as a lipid bilayer begins to form within a cell, $\Delta V_{ADC}$ increases as well. $\Delta V_{ADC}$ is roughly proportional to the capacitance associated with the lipid membrane/bilayer, C(bilayer). An increase in $\Delta V_{ADC}$ can therefore be used as an indicator that a lipid bilayer has been formed within a cell.

In some embodiments, in order to maximize the observable $\Delta V_{ADC}$ for a more reliable detection of a lipid bilayer, $\Delta V_{ADC}$ in response to a maximum voltage change applied to the bulk liquid in contact with the lipid membrane/bilayer (max $\Delta V_{liq}$) is monitored in order to detect whether a lipid bilayer has been formed in a cell.

Figure 8A:
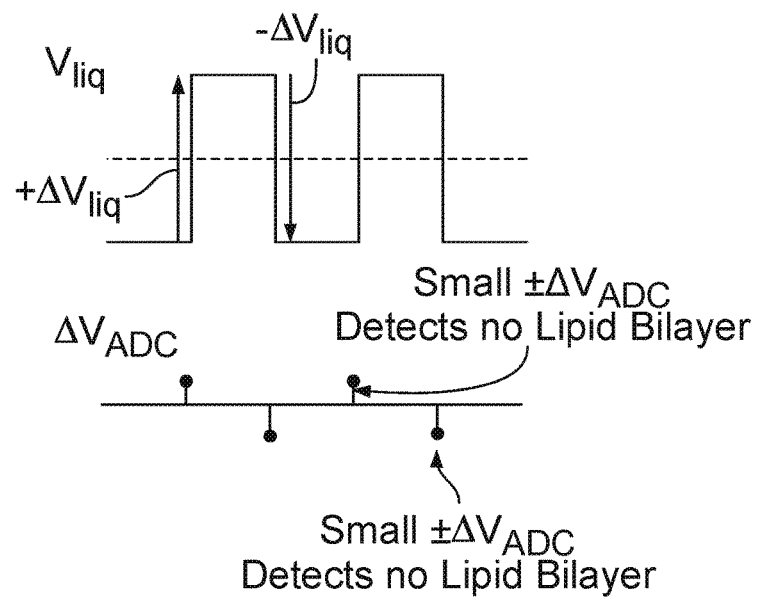
FIG. 8A illustrates that a small observed positive/negative voltage change $\pm\Delta V_{ADC}$ in response to a positive/negative voltage change $\pm\Delta V_{liq}$ detects that no lipid bilayer has been formed in the cell.
Figure 8B:
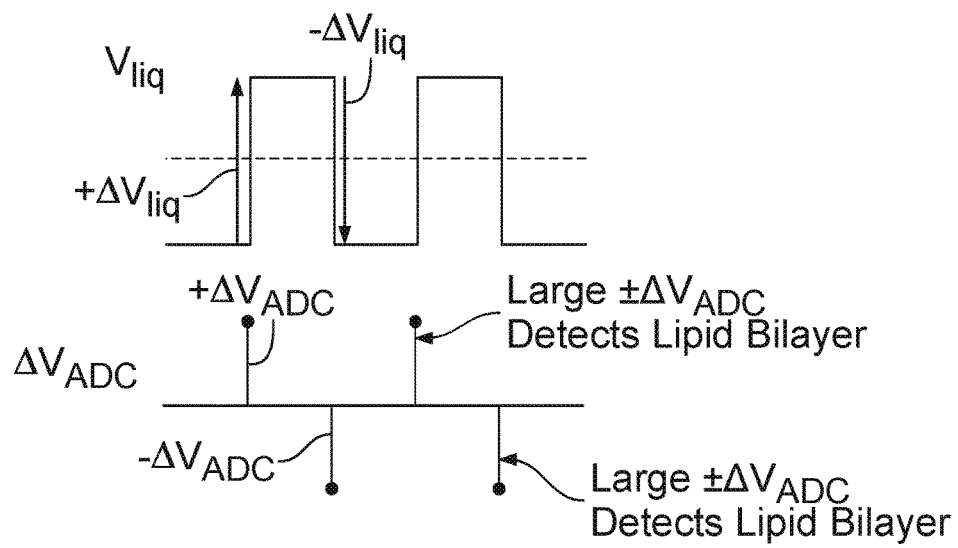
FIG. 8B illustrates that a large observed positive/negative voltage change $\pm\Delta V_{ADC}$ in response to a positive/negative voltage change $\pm\Delta V_{liq}$ detects that a lipid bilayer has been formed in a cell.

FIG. 8A illustrates that a small observed positive/negative voltage change $\pm\Delta V_{ADC}$ in response to a positive/negative voltage change $\pm\Delta V_{liq}$ results in no lipid bilayer being detected to have been formed in the cell. FIG. 8B illustrates that a large observed positive/negative voltage change $\pm\Delta V_{ADC}$ in response to a positive/negative voltage change $\pm\Delta V_{liq}$ results in the detection of a lipid bilayer having been formed in a cell.

In FIG. 8A, a maximum positive voltage change $+\Delta V_{liq}$ occurs when the square wave $V_{liq}$ changes from a negative phase to a positive phase, while a maximum negative voltage change $-\Delta V_{liq}$ occurs when the square wave $V_{liq}$ changes from a positive phase to a negative phase. In FIG. 8A, at the instance when $\Delta V_{liq}$ is at a positive maximum, only a small $+\Delta V_{ADC}$ can be observed if a lipid bilayer has not been formed in the cell; at the instance when $\Delta V_{liq}$ is at a negative maximum, only a small $-\Delta V_{ADC}$ can be observed if a lipid bilayer has not been formed in the cell.

In FIG. 8B, at the instance when $\Delta V_{liq}$ is at a positive maximum, a large positive voltage change $+\Delta V_{ADC}$ can be observed if a lipid bilayer has already been formed in the cell. And at the instance when $\Delta V_{liq}$ is at a negative maximum, a large negative voltage change $-\Delta V_{ADC}$ can be observed if a lipid bilayer has already been formed in the cell.

In some embodiments, the absolute value of $\Delta V_{ADC}$ ($|\Delta V_{ADC}|$) observed when the absolute value of $\Delta V_{liq}$ ($|\Delta V_{liq}|$) is at a maximum is compared with a predetermined threshold. If ($|\Delta V_{ADC}|$>predetermined threshold), then it is determined that a lipid bilayer is detected. Conversely, if ($|\Delta V_{ADC}|$<predetermined threshold), then it is determined that a lipid bilayer is not detected.

Figure 9A:
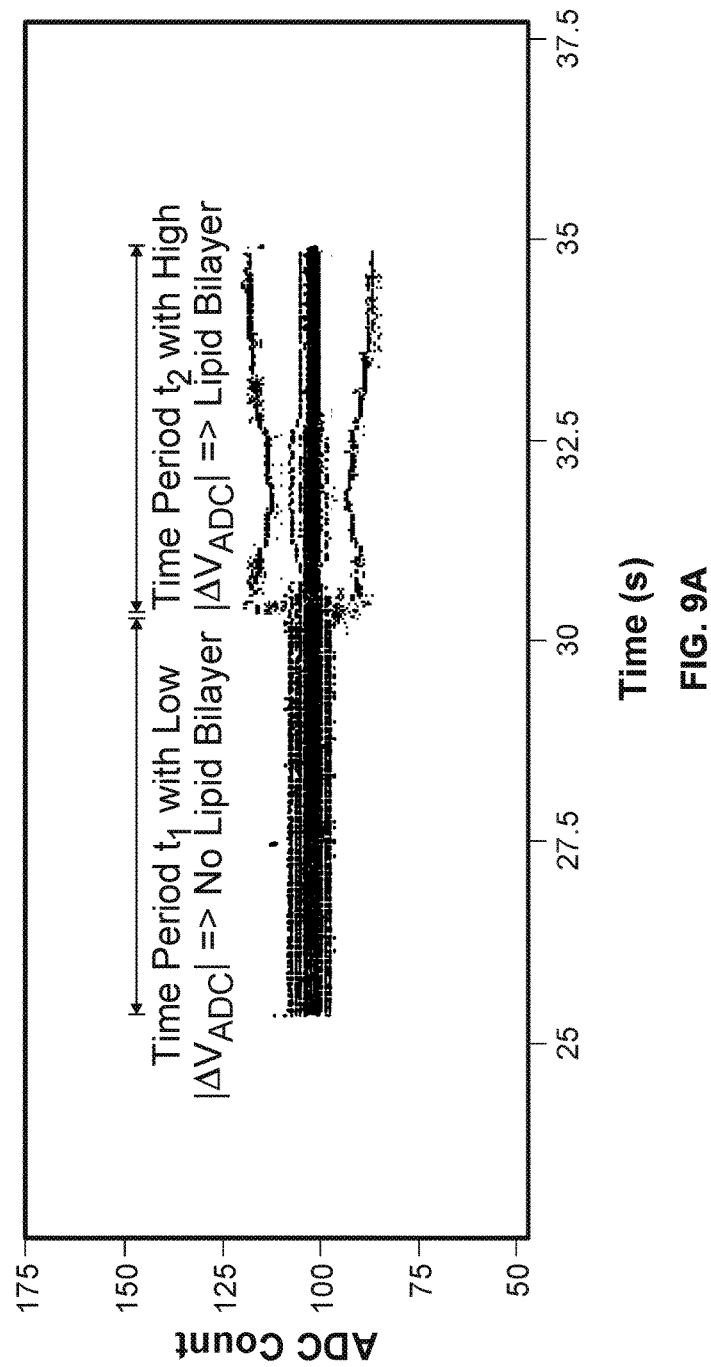
FIG. 9A illustrates an exemplary plot of $V_{ADC}$ versus time before and after a lipid bilayer is formed within a cell.

FIG. 9A illustrates an exemplary plot of $V_{ADC}$ versus time before and after a lipid bilayer is formed within a cell. The plot in FIG. 9A is based on real testing data. As shown in FIG. 9A, the units of $V_{ADC}$ on the y-axis are in ADC counts. However, other units may be used as well. As shown in FIG. 9A, during a time period $t_1$ when a lipid bilayer has not been formed, the recorded $|\Delta V_{ADC}|$ values are smaller than those recorded during a time period $t_2$ after a lipid bilayer has been formed in the cell.

Figure 9B:
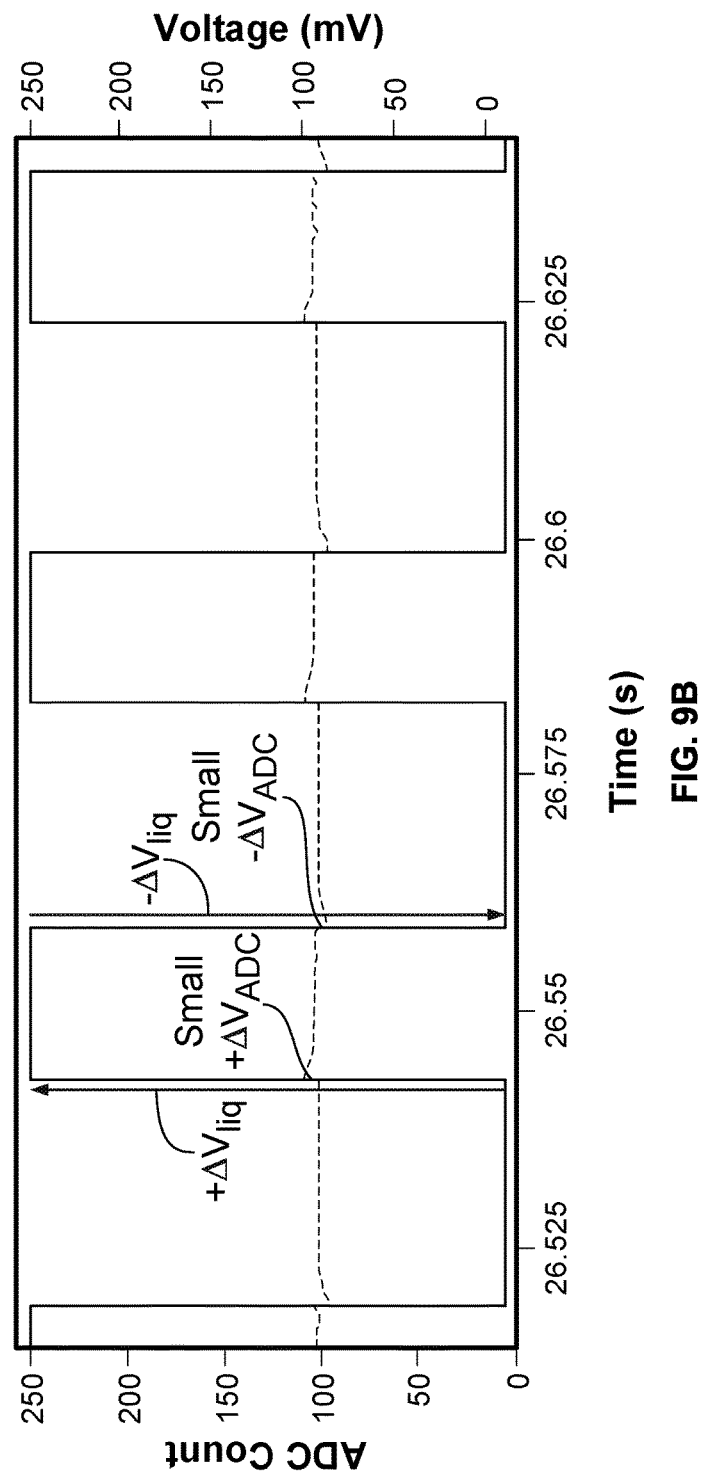
FIG. 9B illustrates a zoomed-in view of the exemplary plot of $V_{ADC}$ versus time (see FIG. 9A) during the time period $t_1$ when a lipid bilayer has not been formed.

FIG. 9B illustrates a zoomed-in view of the exemplary plot of $V_{ADC}$ versus time (see FIG. 9A) during the time period $t_1$ when a lipid bilayer has not been formed. The results shown in FIG. 9B are consistent with FIG. 8A. In FIG. 9B, a maximum $+\Delta V_{liq}$ occurs when the square wave $V_{liq}$ changes from a negative phase to a positive phase, while a maximum $-\Delta V_{liq}$ occurs when the square wave $V_{liq}$ changes from a positive phase to a negative phase. In FIG. 9B, at the instance when $\Delta V_{liq}$ is at a positive maximum, only a small $+\Delta V_{ADC}$ can be observed because a lipid bilayer has not been formed in the cell; at the instance when $\Delta V_{liq}$ is at a negative maximum, only a small $-\Delta V_{ADC}$ can be observed because a lipid bilayer has not been formed in the cell.

Figure 9C:
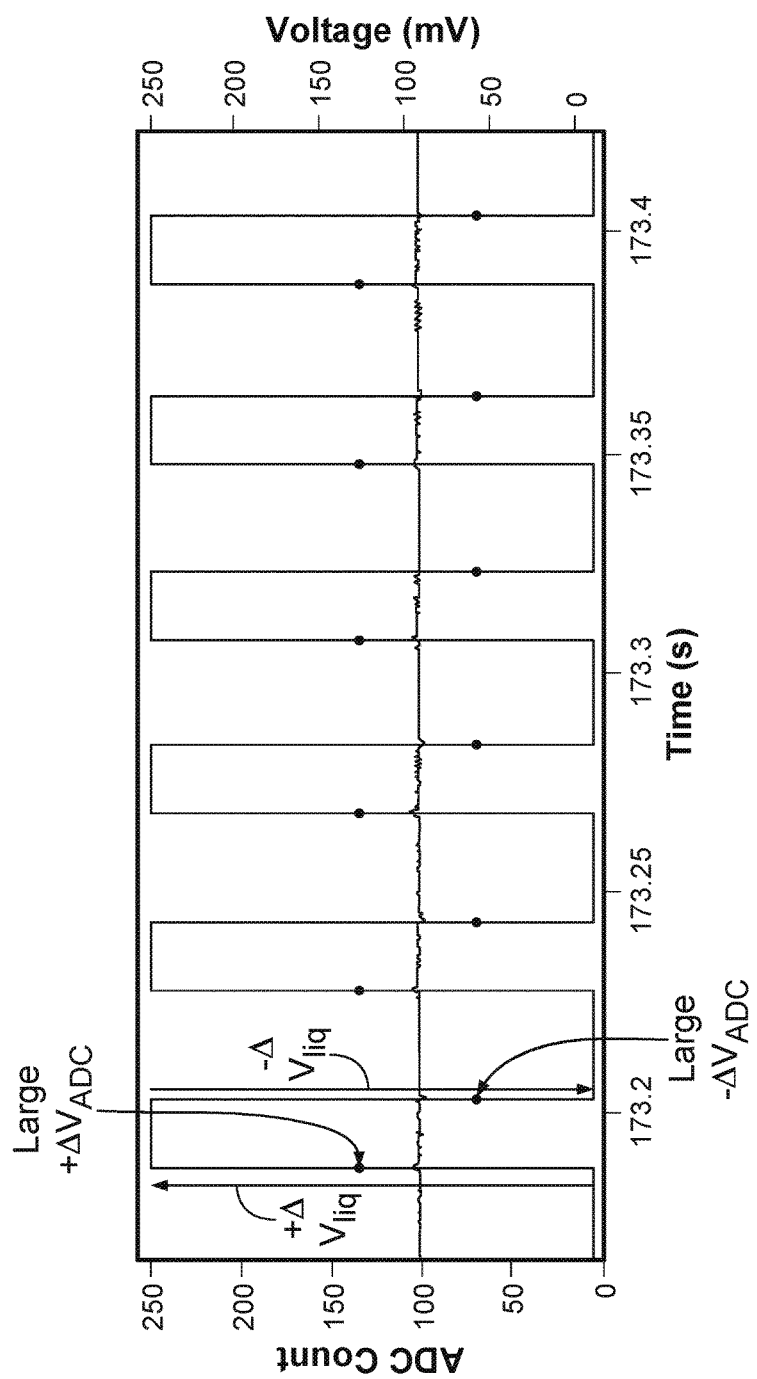
FIG. 9C illustrates a zoomed-in view of the exemplary plot of $V_{ADC}$ versus time (see FIG. 9A) during the time period $t_2$ when a lipid bilayer has been formed.

FIG. 9C illustrates a zoomed-in view of the exemplary plot of $V_{ADC}$ versus time (see FIG. 9A) during the time period $t_2$ when a lipid bilayer has been formed. The results shown in FIG. 9C are consistent with FIG. 8B. In FIG. 9C, at the instance when $\Delta V_{liq}$ is at a positive maximum, a large $+\Delta V_{ADC}$ can be observed between two consecutive sample points because a lipid bilayer has already been formed in the cell. At the instance when $\Delta V_{liq}$ is at a negative maximum, a large $-\Delta V_{ADC}$ can be observed because a lipid bilayer has already been formed in the cell. Note that shortly after the square wave $V_{liq}$ changes from one phase to another, $\Delta V_{liq}$ stays at zero, and $V_{ADC}$ reduces to zero in response. As shown in FIG. 9C, when a lipid bilayer has already been formed in the cell, a positive or negative spike in $V_{ADC}$ can be observed. The positive or negative spikes are followed by much smaller $V_{ADC}$ values.

After it is determined that a lipid bilayer has been properly formed within a cell of the nanopore based sequencing chip using the above described technique, a nanopore may be inserted into the lipid bilayer, and the cell with the inserted nanopore may be used for nucleic acid sequencing. During the sequencing phase, the lipid bilayers in some of the cells in the nanopore based sequencing chip may rupture due to osmotic imbalance or other reasons. A ruptured lipid bilayer in a cell is undesirable because it causes a very high current to flow across the electrodes as a result of a short-circuit like condition, and the high current may also affect data acquisition in neighboring cells. Therefore, a technique for detecting during the sequencing phase a cell that has a short-circuit condition due to a ruptured lipid bilayer is desirable. The technique enables the nanopore based sequencing chip to disable the detected cell, thereby improving the overall performance of the chip.

Disabling a cell with a short-circuit condition may be achieved by controlling pass device 606 as shown in FIG. 6A or FIG. 6B. Pass device 606 may be used as a switch to disable the cell by disconnecting the electrodes from the measurement circuitry 600, such that a voltage stimulus is no longer applied across the ruptured lipid bilayer/membrane in the cell.

Detecting a cell with a short-circuit condition during the sequencing phase may be achieved by using circuitry 600 to monitor a delta voltage change, $\Delta V_{ADC}$, at integrating capacitor 608 ($n_{cap}$) in response to a delta voltage change ($\Delta V_{liq}$) applied to the bulk liquid in contact with the lipid membrane/bilayer, which is similar to the technique described above for detecting the formation of a lipid bilayer in a cell. As will be described in greater detail below, during the sequencing phase, circuitry 600 may be modeled as a voltage divider with $n_{cap}$ connected in series with an impedance Z 1002 associated with the working electrode and the lipid bilayer/membrane, which is similar to model 7000 described earlier for modeling circuitry 600 during the lipid bilayer measurement phase. A voltage change tapped at an intermediate point of the voltage divider can be read by ADC 610 for determining whether there is a short-circuit condition due to a ruptured lipid bilayer in the cell.

Figure 10:
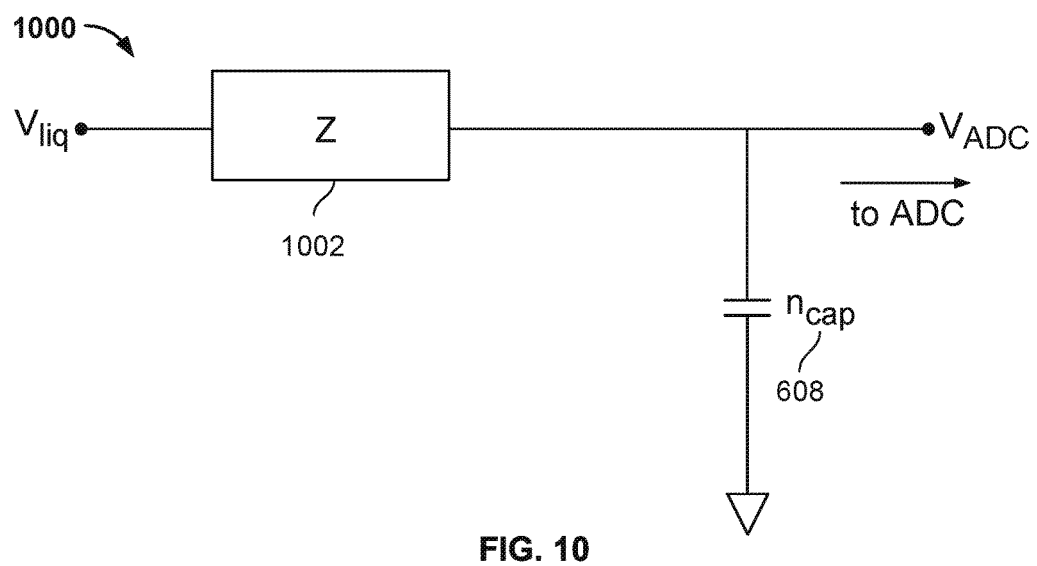
FIG. 10 illustrates an electrical model 1000 representing the electrical properties of a portion of circuitry 600 during the sequencing phase of the system.

FIG. 10 illustrates an electrical model 1000 representing the electrical properties of a portion of circuitry 600 during the sequencing phase of the system. As shown in FIG. 10, an impedance Z 1002 is used to model the working electrode and lipid bilayer/membrane, and Z 1002 is connected in series with $n_{cap}$ 608.

When operating in an AC mode, the voltage read by the ADC ($V_{ADC}$) can be determined by:

$$V_{ADC} = V_{liq} * \frac{Z(ncap)}{Z1002 + Z(ncap)} \quad \text{Equation (4)}$$

where $Z=1/(j\omega C)$,

Z(ncap) is the AC impedance associated with $n_{cap}$, and Z 1002 is the AC impedance associated with the working electrode and the lipid bilayer/membrane.

In Equation (4) above, as the lipid bilayer ruptures, Z 1002 decreases significantly because of the short-circuited condition, such that $V_{ADC}$ has a value that is close to $V_{liq}$. A further increase in $V_{ADC}$ can therefore be used as an indicator that a lipid bilayer has been ruptured within a cell.

In some embodiments, a delta voltage change $\Delta V_{ADC}$ at integrating capacitor 608 ($n_{cap}$) in response to a delta voltage change ($\Delta V_{liq}$) applied to the bulk liquid in contact with the lipid membrane/bilayer is monitored in order to detect whether a lipid bilayer has been ruptured in a cell. For example, Equation (4) may be rewritten as:

$$\Delta V_{ADC} = \Delta V_{liq} * \frac{Z(ncap)}{Z1002 + Z(ncap)} \quad \text{Equation (5)}$$

where $\Delta V_{ADC}$ is a voltage change at integrating capacitor 608 ($n_{cap}$) read by the ADC, $\Delta V_{liq}$ is a voltage change applied to the bulk liquid, Z(ncap) is the AC impedance associated with $n_{cap}$, and Z 1002 is the AC impedance associated with working electrode and the lipid bilayer/membrane.

In Equation (5) above, because Z 1002 decreases as the lipid bilayer ruptures within a cell, $\Delta V_{ADC}$ increases to a value that is close to $\Delta V_{liq}$. A further increase in $\Delta V_{ADC}$ can therefore be used as an indicator that a lipid bilayer has just been ruptured within a cell.

In some embodiments, in order to maximize the observable $\Delta V_{ADC}$ for a more reliable detection of a ruptured lipid bilayer, $\Delta V_{ADC}$ in response to a maximum voltage change applied to the bulk liquid in contact with the lipid membrane/bilayer (max $\Delta V_{liq}$) is monitored in order to detect whether a lipid bilayer has just been ruptured in a cell.

Figure 11A:
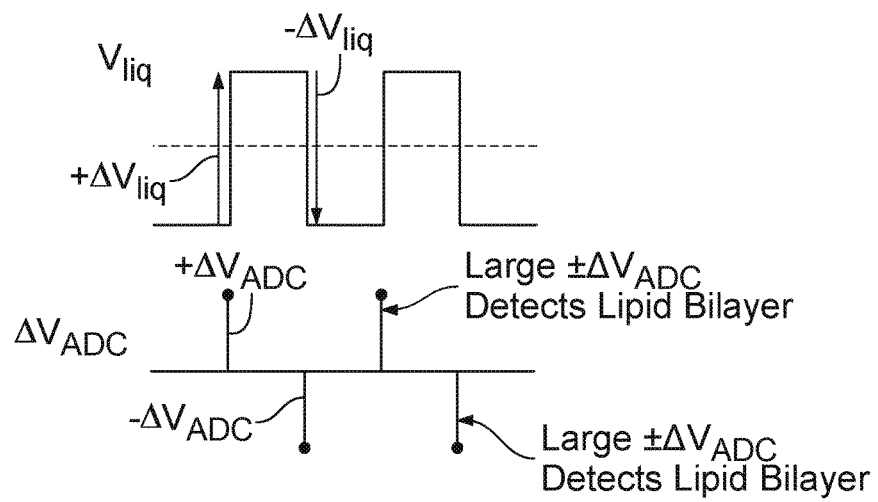
FIG. 11A illustrates that a large observed positive/negative voltage change $\pm\Delta V_{ADC}$ in response to a positive/negative voltage change $\pm\Delta V_{liq}$ indicates that a lipid bilayer is still intact in a cell.
Figure 11B:
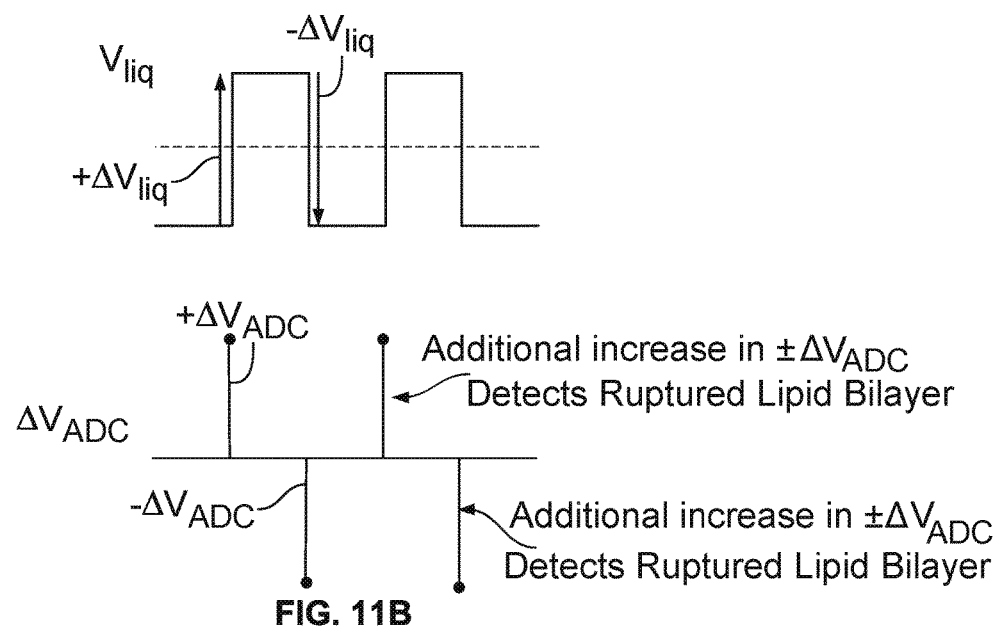
FIG. 11B illustrates that a further increase in the observed positive/negative voltage change $\pm\Delta V_{ADC}$ in response to a positive/negative voltage change $\pm\Delta V_{liq}$ indicates that a lipid bilayer has just been ruptured in the cell.

FIG. 11A illustrates that a large observed positive/negative voltage change $\pm\Delta V_{ADC}$ in response to a positive/negative voltage change $\pm\Delta V_{liq}$ indicates that a lipid bilayer is still intact in a cell. FIG. 11A is identical to FIG. 8B. FIG. 11B illustrates that a further increase in the observed positive/negative voltage change $\pm\Delta V_{ADC}$ in response to a positive/negative voltage change $\pm\Delta V_{liq}$ indicates that a lipid bilayer has just been ruptured in the cell.

In FIG. 11B, at the instance when $\Delta V_{liq}$ is at a positive maximum, a further increase in magnitude of a positive voltage change $+\Delta V_{ADC}$ can be observed if a lipid bilayer has just been ruptured in the cell. And at the instance when $\Delta V_{liq}$ is at a negative maximum, a further increase in magnitude of a negative voltage change $-\Delta V_{ADC}$ can be observed if a lipid bilayer has just been ruptured in the cell.

In view of FIGS. 8A, 8B, 11A, and 11B, the absolute value of $\Delta V_{ADC}$ ($|\Delta V_{ADC}|$) observed when the absolute value of $\Delta V_{liq}$ ($|\Delta V_{liq}|$) is at a maximum may be compared with one or more predetermined thresholds in order to determine the state of a lipid membrane. For example, two threshold levels may be used to determine the state of a lipid membrane, where threshold1<threshold2. If ($|\Delta V_{ADC}|$<threshold1), then it is determined that the lipid membrane has multiple layers of lipid molecules and solvent combined together, and is not yet a lipid bilayer. If ((threshold1<=$|\Delta V_{ADC}|$<threshold2), then it is determined that a lipid bilayer is formed. If ($|\Delta V_{ADC}|$>=threshold2), then it is determined that a lipid bilayer is ruptured.

However, applying the above described diagnostic technique to detect a ruptured lipid bilayer in a cell of a nanopore based sequencing chip during the sequencing phase of the system has a number of challenges. One of the challenges is selecting a suitable ADC reference window and a suitable $V_{liq}$ magnitude that work well for both nucleic acid sequencing (the main experiment) and the diagnostic test. An ADC reference window is the range of minimum to maximum analog values that the ADC can convert. The ADC reference window specifies the full scale measurement range, such as $-V_{ref}$ to $+V_{ref}$ millivolts/volts, and is programmable on the ADC chip. During the sequencing phase of the nanopore based sequencing chip, the signal useful for nucleic acid sequencing is very small, and therefore the ADC reference window is programmed to a small voltage window, such that the small signal may be resolved into different discrete levels. However the $|\Delta V_{ADC}|$ in response to a phase change of the square wave $V_{liq}$ for a cell with a ruptured lipid bilayer is considerably larger than the signal useful for nucleic acid sequencing. As a result, a small ADC reference window that is suitable for nucleic acid sequencing may likely cause the $\Delta V_{ADC}$ signal read by the ADC to saturate. Lowering the $V_{liq}$ magnitude to prevent the saturation of the $\Delta V_{ADC}$ signal is not a viable solution because the $V_{liq}$ magnitude is constrained by the biochemistry for nucleic acid sequencing. Consequently, the diagnostic technique described above may no longer reliably distinguish between an intact lipid bilayer and a ruptured one in a cell, especially when the modulation frequency of $V_{liq}$ is beyond a certain threshold level, e.g., 80 Hz or 100 Hz. Therefore, improved techniques to detect a state of a lipid membrane in a cell of a nanopore based sequencing chip during different phases of the system would be desirable.

Figure 12:
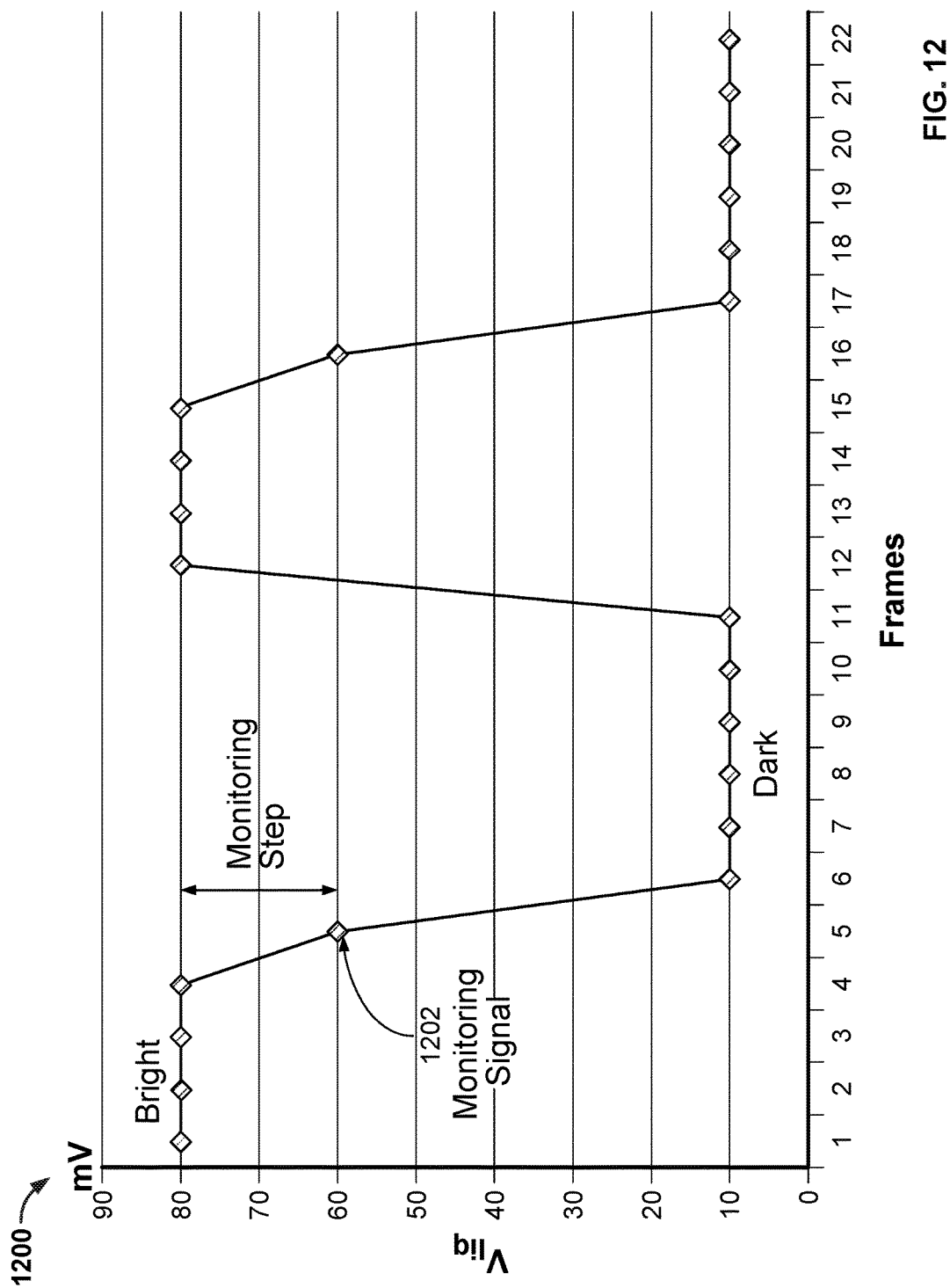
FIG. 12 illustrates an exemplary plot of an improved $V_{liq}$ waveform 1200 for detecting a state of a lipid membrane in a cell of a nanopore based sequencing chip during different phases (including the sequencing phase) of the system.

FIG. 12 illustrates an exemplary plot of an improved $V_{liq}$ waveform 1200 for detecting a state of a lipid membrane in a cell of a nanopore based sequencing chip during different phases (including the sequencing phase) of the system. The states include a lipid membrane with multiple layers of lipid molecules and solvent combined together, a lipid bilayer, and a ruptured lipid bilayer. The improved $V_{liq}$ waveform 1200 may be applied to circuitry 600 in FIG. 6A. Unlike the original $V_{liq}$ waveform, which is a square wave that switches between two magnitudes when the waveform changes from a positive phase to a negative phase, or vice versa (e.g., see FIG. 11B), the improved $V_{liq}$ waveform 1200 includes an additional monitoring signal 1202. In FIG. 12, the x-axis plots the frames and the y-axis plots the $V_{liq}$ waveform in units of mV. In this particular embodiment, the additional monitoring signal 1202 is inserted when $V_{liq}$ waveform 1200 switches from a bright period to a dark period. In particular, $V_{liq}$ switches from the bright magnitude (80 mV at frame #4 or #15) to an intermediate monitoring signal magnitude (60 mV at frame #5 or #16) before it switches to the dark magnitude (10 mV at frame #6 or #17). An intermediate change in the $V_{liq}$ AC voltage is inserted between two magnitudes of the AC voltage, the bright magnitude and the dark magnitude. In some other embodiments, the additional monitoring signal is inserted when the waveform switches from a dark period to a bright period. In these embodiments, $V_{liq}$ switches from the dark magnitude level to an intermediate monitoring signal magnitude before it switches to the bright magnitude level. The intermediate monitoring signal magnitude may be a small delta in voltage (e.g., −20 mV, as shown in FIG. 12) from the voltage level prior to the monitoring signal. An intermediate change in the $V_{liq}$ AC voltage is inserted between two magnitudes of the AC voltage, the dark magnitude and the bright magnitude. In some embodiments, the delta change in voltage may be a fraction (e.g., 2/7, as shown in FIG. 12) of the total change in magnitude of $V_{liq}$ when the waveform switches between phases. In FIG. 12, the magnitude change of $V_{liq}$ waveform 1200 from a bright period to a dark period is 70 mV. In other embodiments, the magnitude range may be smaller or larger, e.g., from 50 mV to 500 mV, depending on the biochemistry for nucleic acid sequencing. The sampling or frame rate may range from 1-10 kHz.

Figure 13:
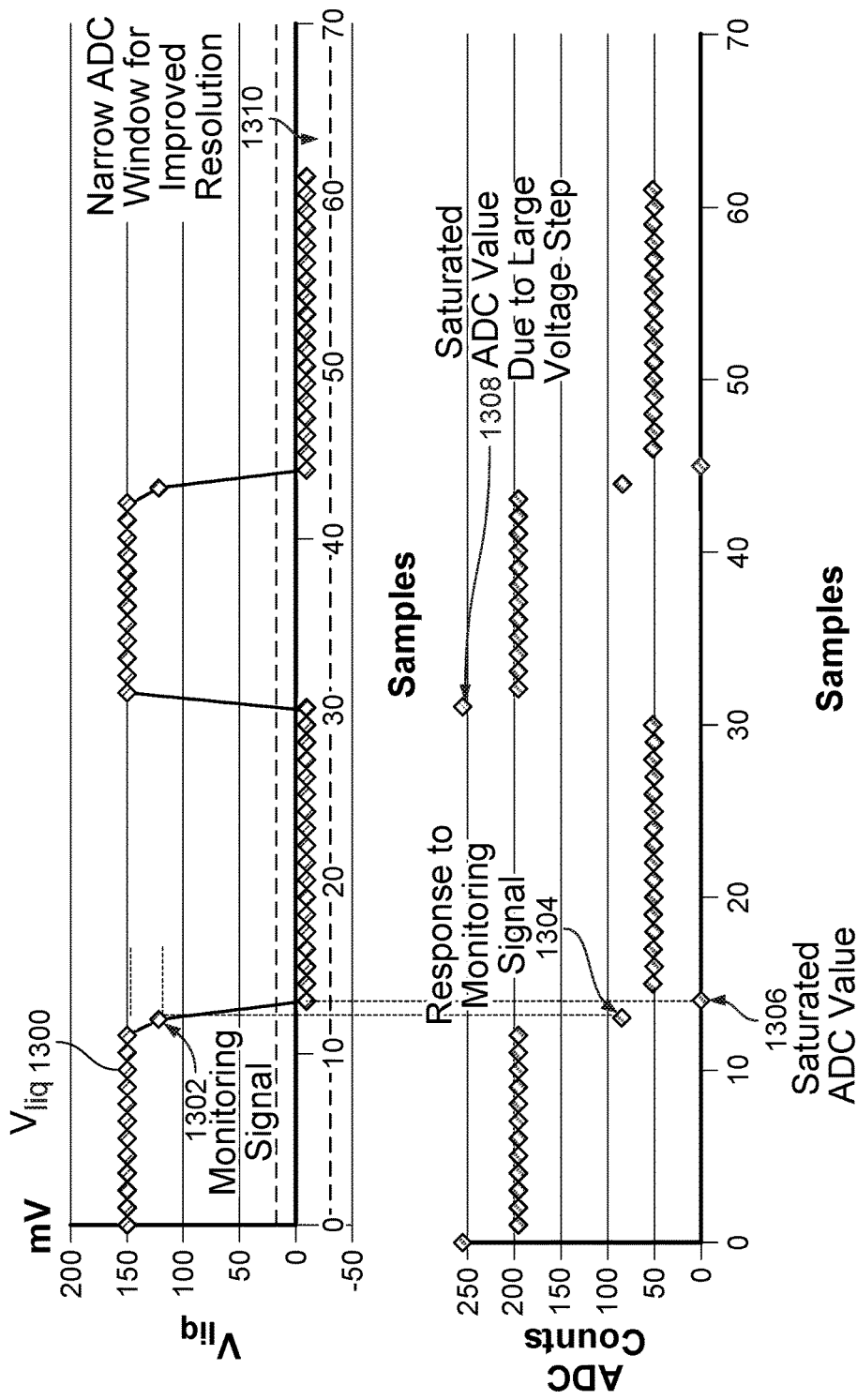
FIG. 13 illustrates that to detect a cell with a short-circuit condition during the sequencing phase, circuitry 600 may monitor a delta voltage change, $\Delta V_{ADC}$, at integrating capacitor 608 ($n_{cap}$) in response to a delta voltage change ($\Delta V_{liq}$) applied to the bulk liquid in contact with the lipid membrane/bilayer when $V_{liq}$ switches from a bright magnitude to a monitoring signal magnitude.

FIG. 13 illustrates that to detect a cell with a short-circuit condition during the sequencing phase, circuitry 600 may monitor a delta voltage change, $\Delta V_{ADC}$, at integrating capacitor 608 ($n_{cap}$) in response to a delta voltage change ($\Delta V_{liq}$) applied to the bulk liquid in contact with the lipid membrane/bilayer when $V_{liq}$ switches from a bright magnitude to a monitoring signal magnitude. In the top plot of FIG. 13, the x-axis plots the frames and the y-axis plots the $V_{liq}$ waveform 1300 in units of mV. In the bottom plot of FIG. 13, the x-axis plots the ADC samples and the y-axis plots the ADC counts read by the ADC at integrating capacitor 608. As shown in the top plot, a narrow ADC reference window 1310 (−25 mV to +25 mV) is programmed on the ADC for an improved resolution for the relatively small signal that is used for nucleic acid sequencing. The narrow ADC reference window 1310 causes the ADC value 1306 and ADC value 1308 to saturate at 0 and 255 count, respectively. However, because the monitoring signal 1302 introduces a voltage change that is only a fraction of the total change in magnitude of $V_{liq}$ when the waveform switches between phases, the response to the monitoring signal 1304 does not saturate and the corresponding delta voltage change may be used to more reliably detect whether the lipid bilayer is intact or ruptured. For example, two threshold levels may be used to determine the state of a lipid membrane, where threshold1<threshold2. If ($|\Delta V_{ADC}|$<threshold)), then it is determined that the lipid membrane has multiple layers of lipid molecules and solvent combined together, and is not yet a lipid bilayer. If ((threshold1<=$|\Delta V_{ADC}|$<threshold2), then it is determined that a lipid bilayer is intact. If ($|\Delta V_{ADC}|$>=threshold2), then it is determined that a lipid bilayer is ruptured.

As shown in FIG. 13, the delta change in voltage introduced by monitoring signal 1302 is about 1/5 of the total change in magnitude of $V_{liq}$ when the waveform switches between phases. However, depending on the ADC reference window selected, the monitoring signal magnitude may be scaled to any appropriate fraction of the total change in magnitude of $V_{liq}$ when the $V_{liq}$ waveform switches between phases, provided that the response to the monitoring signal remains unsaturated.

In some embodiments of the nanopore based sequencing chip, the nanopore array is divided into cell banks. For example, each cell bank may include M rows×N columns of cells. Row and column select lines are used to control the states of the individual cells. M and N may be any integer numbers. For example, a cell bank that is 8k in size (referred to as a bank8k) may be configured as 64 rows by 128 columns, with a total of 64×128 cells. Since each cell bank is autonomous, the nanopore array may be scaled by adding additional banks. For example, a 128k array may be implemented as sixteen bank8k elements. A 512k array may be implemented as an 8×8 array of bank8k elements. In some embodiments, the nanopore array may be scaled to include millions of cells.

In some embodiments, the cells in any given row of a cell bank share the same integration time interval, i.e., each of the cells in the same row starts and ends its integration at the same time, and the integration time intervals of adjacent rows are staggered from one another. Because the integration time intervals of adjacent rows are offset in time from each other, the detection technique using the monitoring signal described above has a row dependence effect, and the overall performance of the detection technique is degraded as a result. As will be described in greater detail below, the row dependence effect may be mitigated by introducing a global pre-charge signal for synchronizing the integration of the cells in different rows of the cell bank when $V_{liq}$ is about to switch to the monitoring signal, thereby improving the overall performance of the detection technique.

Figure 14:
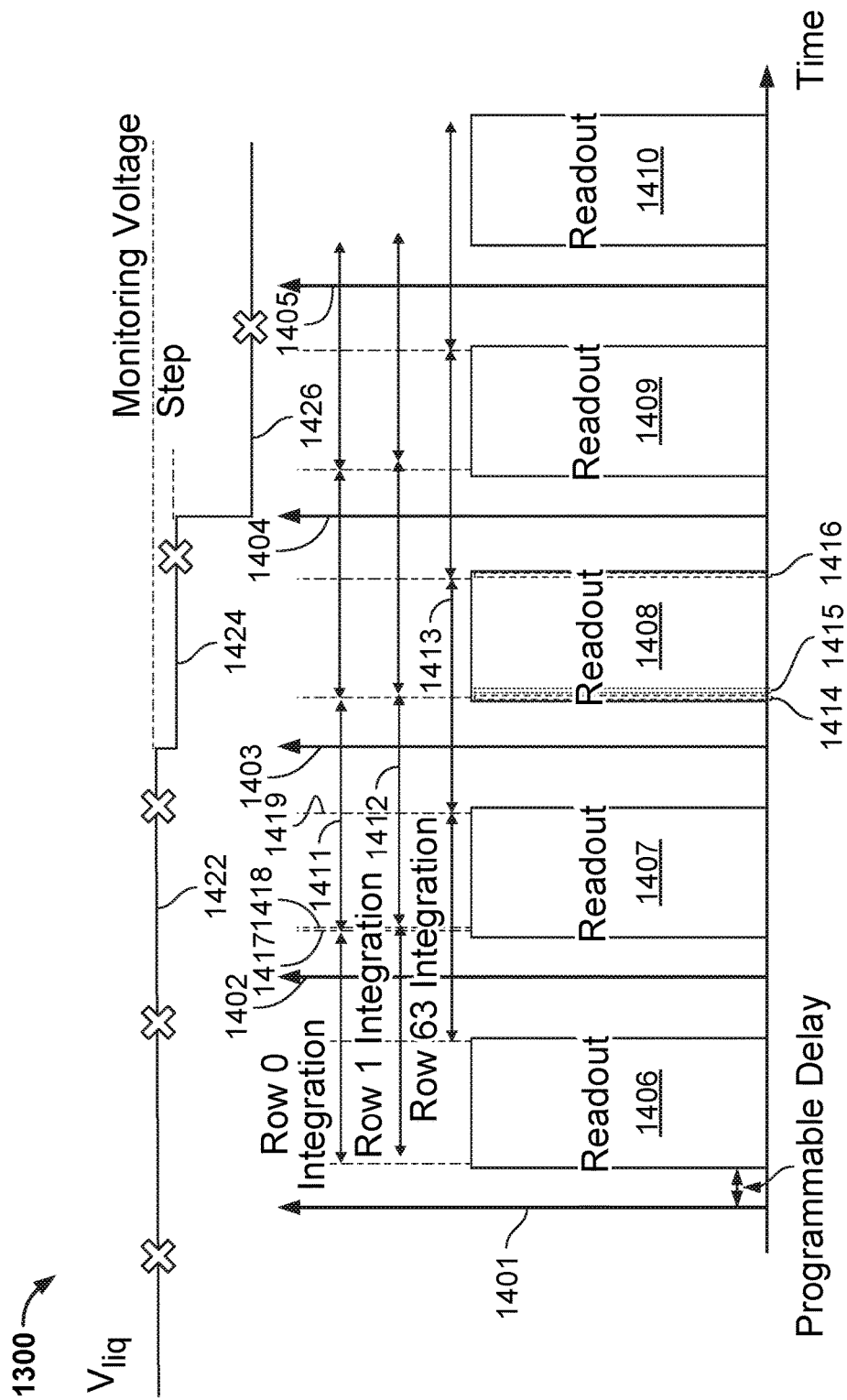
FIG. 14 illustrates that the cells in any given row of a cell bank share the same integration time intervals, but that the integration time intervals of adjacent rows are staggered from each other, causing a row dependence effect which degrades the overall performance of the detection of ruptured lipid bilayers.

FIG. 14 illustrates that the cells in any given row of a cell bank share the same integration time intervals, but that the integration time intervals of adjacent rows are staggered from each other, causing a row dependence effect which degrades the overall performance of the detection of states of lipid membranes. The top part of FIG. 14 shows the zoomed-in version of $V_{liq}$ waveform 1300 (see FIG. 13). $V_{liq}$ 1300 starts at a bright magnitude 1422 and switches to an intermediate monitoring signal magnitude 1424 before switching to a dark magnitude 1426.

The bottom part of FIG. 14 shows a timing diagram that indicates the frames, the integration time intervals for different rows (e.g., row 0, row 1, and row 63) of the cell bank, and the readout timing of the ADCs.

The vertical arrows 1401-1405 define the beginning of the frames of $V_{liq}$ waveform 1300; they are the time instances when the system may determine whether to maintain the $V_{liq}$ magnitude at its current value or switch to a different value. At frames 1401 and 1402, $V_{liq}$ 1300 is maintained at bright magnitude 1422. At frame 1403, $V_{liq}$ 1300 switches to intermediate monitoring signal magnitude 1424. At frame 1404, $V_{liq}$ 1300 switches to dark magnitude 1426. And at frame 1405, $V_{liq}$ 1300 is maintained at dark magnitude 1426.

Each of the horizontal arrows indicates the integration time interval of the cells in a particular row of the cell bank. For example, the top set of horizontal arrows indicate the integration time intervals of the cells in row 0, the second set of horizontal arrows indicate the integration time intervals of the cells in row 1, and the bottom set of horizontal arrows indicate the integration time intervals of the cells in row 63. As shown in the figure, the integration time intervals of adjacent rows are offset in time from each other. For example, the beginning of an integration time interval for row 0 and the beginning of an integration time interval for row 1 are offset by a small delta time difference; the beginning of an integration time interval for row 1 and the beginning of an integration time interval for row 2 are offset by a small delta time difference, and so on.

The cells in any given row of a cell bank share the same integration time interval, but the integration time intervals of adjacent rows are staggered from each other because the timing of the reset signal 603 used to trigger the pre-charging of the integrating capacitors 608 (see FIG. 6A) for cells in one row is different from those for other rows.

For example, at time 1417, each of the cells in row 0 has its reset signal 603 closing the cell's switch 601, such that its integrating capacitor 608 is connected to voltage source $V_{pre}$ 605. After integrating capacitor 608 is pre-charged, reset signal 603 is used to open switch 601 such that integrating capacitor 608 is disconnected from voltage source $V_{pre}$ 605. At this point, integrating capacitor 608 starts to discharge and the integration time interval 1411 for row 0 begins. After the integration time interval 1411 for row 0 is over, the voltage stored in integrating capacitor 608 of each of the cells in row 0 may be read out by ADC 610 at time 1414. After the sampling by ADC 610, integrating capacitor 608 is pre-charged again by using reset signal 603 to close switch 601, such that integrating capacitor 608 is connected to voltage source $V_{pre}$ 605 again. The steps of pre-charging the integrating capacitor 608, waiting a fixed period of time for the integrating capacitor 608 to integrate, and sampling the voltage stored in integrating capacitor 608 by ADC 610 are then repeated in cycles.

The reset signal 603 used to trigger the pre-charging and integration of the cells in row 1 lags behind that of row 0 by a small delta time difference, at time 1418. After the integration time interval 1412 for row 1 is over, the voltage stored in integrating capacitor 608 of each of the cells in row 1 may be read out by ADC 610 at time 1415. Similarly, the reset signal 603 used to trigger the pre-charging and integration of the cells in row 1 lags behind that of row 2 by a small delta time difference, the reset signal 603 of the cells in row 3 lags behind that of row 2 by a small delta time difference, and so on. This pattern is repeated until row 63. In particular, at time 1419, each of the cells in row 63 has its reset signal 603 triggering the pre-charging and integration of the cells. After the integration time interval 1413 for row 63 is over, the voltage stored in integrating capacitor 608 of each of the cells in row 63 is read out by ADC 610 at time 1416.

Because the integration time intervals of different rows of cells are offset in time, when $V_{liq}$ 1300 switches from bright magnitude 1422 to intermediate monitoring signal magnitude 1424, the cells in two different rows experience the monitoring voltage change at different times within their respective integration time intervals, thereby causing the ADC outputs of the two different rows to differ. For example, the cells in row 0 experience the monitoring voltage change at the latter part of integration time interval 1411, while the cells in row 63 experience the monitoring voltage change at the earlier part of integration time interval 1413; therefore, the ADC outputs in row 0 versus those in row 63 have greater variations than the ADC outputs in the same row, thereby causing the row dependence effect.

Figure 15:
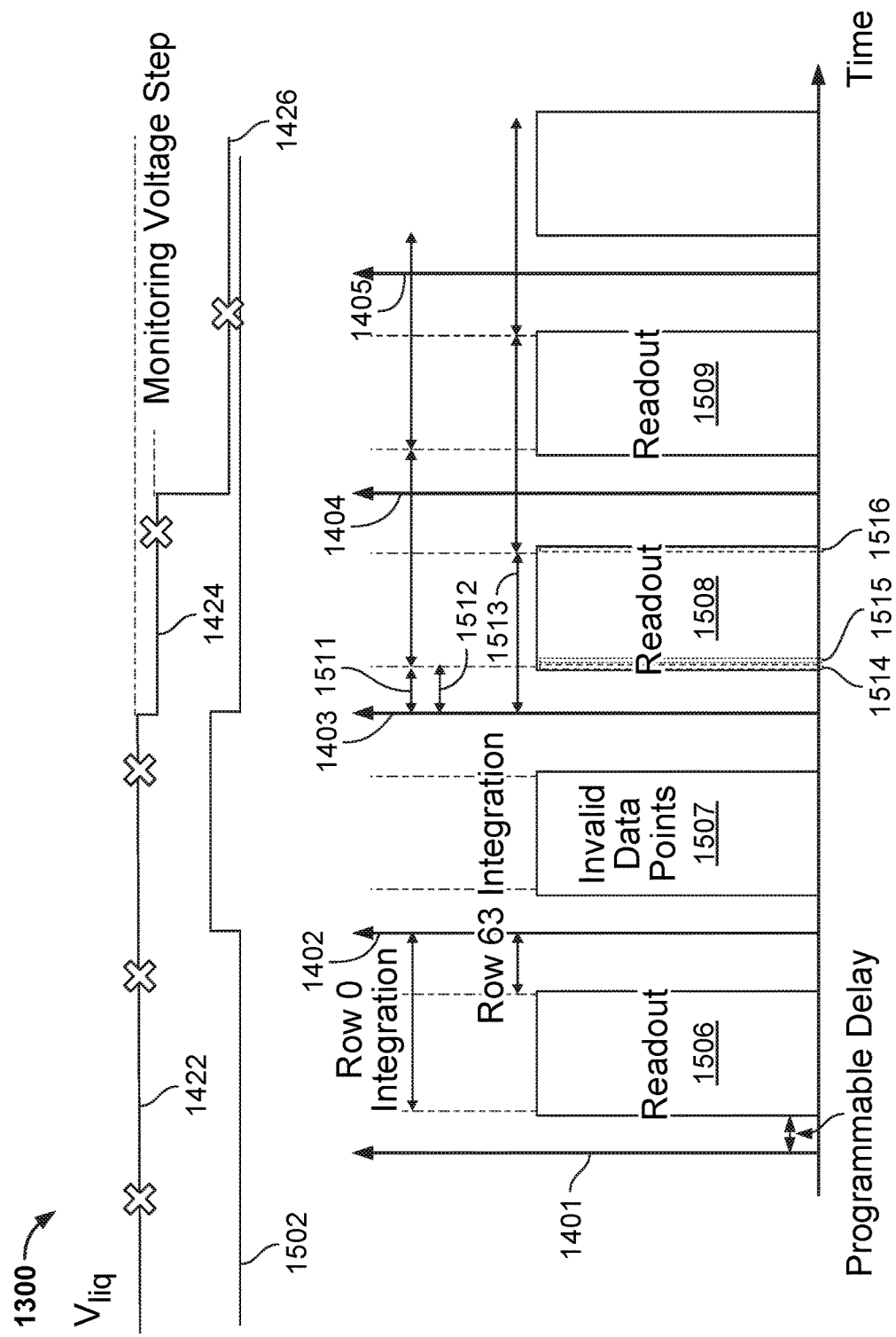
FIG. 15 illustrates that a global pre-charge signal 1502 is used to synchronize the integration of the cells in different rows of the cell bank when $V_{liq}$ is about to switch to the intermediate monitoring signal.

FIG. 15 illustrates that a global pre-charge signal 1502 is used to synchronize the integration of the cells in different rows of the cell bank when $V_{liq}$ is about to switch to the intermediate monitoring signal. FIG. 14 and FIG. 15 are similar apart from a few differences: one difference is the introduction of the global pre-charge signal 1502, as will be described in greater detail below; another difference is that in FIG. 15, the integration time intervals of adjacent rows are no longer staggered from each other the way they are in FIG. 14 (see integration time intervals 1511, 1512, and 1513) when $V_{liq}$ 1300 is switched to intermediate monitoring signal magnitude 1424. For example, the beginning of integration time interval 1511 for row 0, the beginning of integration time interval 1512 for row 1, and the beginning of integration time interval 1513 for row 63 now occur at the same time.

Global pre-charge signal 1502 is a pre-charge signal that is used to control switch 601 across all of the cells in a cell bank. In contrast, reset signal 603 is a pre-charge signal that is used to control switch 601 in a single cell or only cells in a single row of the cell bank. As shown in FIG. 15, global pre-charge signal 1502 is set to high at frame 1402 (the frame before $V_{liq}$ 1300 is switched to intermediate monitoring magnitude 1424), which closes all the switches 601 in the cells of the cell bank, such that all the integrating capacitors 608 are connected to voltage source $V_{pre}$ 605 and pre-charged to the $V_{pre}$ voltage level. Global pre-charge signal 1502 is then set to low at frame 1403 (the frame when $V_{liq}$ 1300 is switched to intermediate monitoring magnitude 1424), which opens all the switches 601 in the cells of the cell bank, such that all integrating capacitors 608 are disconnected from voltage source $V_{pre}$ 605 and start to discharge and integrate at the same time (see integration time intervals 1511, 1512, and 1513).

After the integration time interval 1511 for row 0 is over, the voltage stored in integrating capacitor 608 of each of the cells in row 0 may be read out by ADC 610 at time 1514. After row 0 is read, the integration time interval 1512 for row 1 is over, and the voltage stored in integrating capacitor 608 of each of the cells in row 1 may be read out by ADC 610 at time 1515. Similarly, the subsequent rows are read out one by one, until row 63 is read out at time 1516.

Although the length of the integration time intervals for different rows are not identical (for example, the lengths of 1511, 1512, and 1513 are different) when $V_{liq}$ 1300 is at intermediate monitoring signal magnitude 1424, all of the cells—irrespective of which row they belong to—integrate while the $V_{liq}$ magnitude is maintained at intermediate monitoring signal magnitude 1424. As a result, the ADC outputs in different rows have less variance, thereby reducing the row dependence effect.

However, one drawback of using the global pre-charge signal 1502 is that one set of sequencing data is lost when global pre-charge signal 1502 is set high between 1402 and 1403. Data points 1507 are invalid because the voltage stored in integrating capacitor 608 of all the cells in the cell bank are pre-charged to the $V_{pre}$ voltage level.

Figure 16:
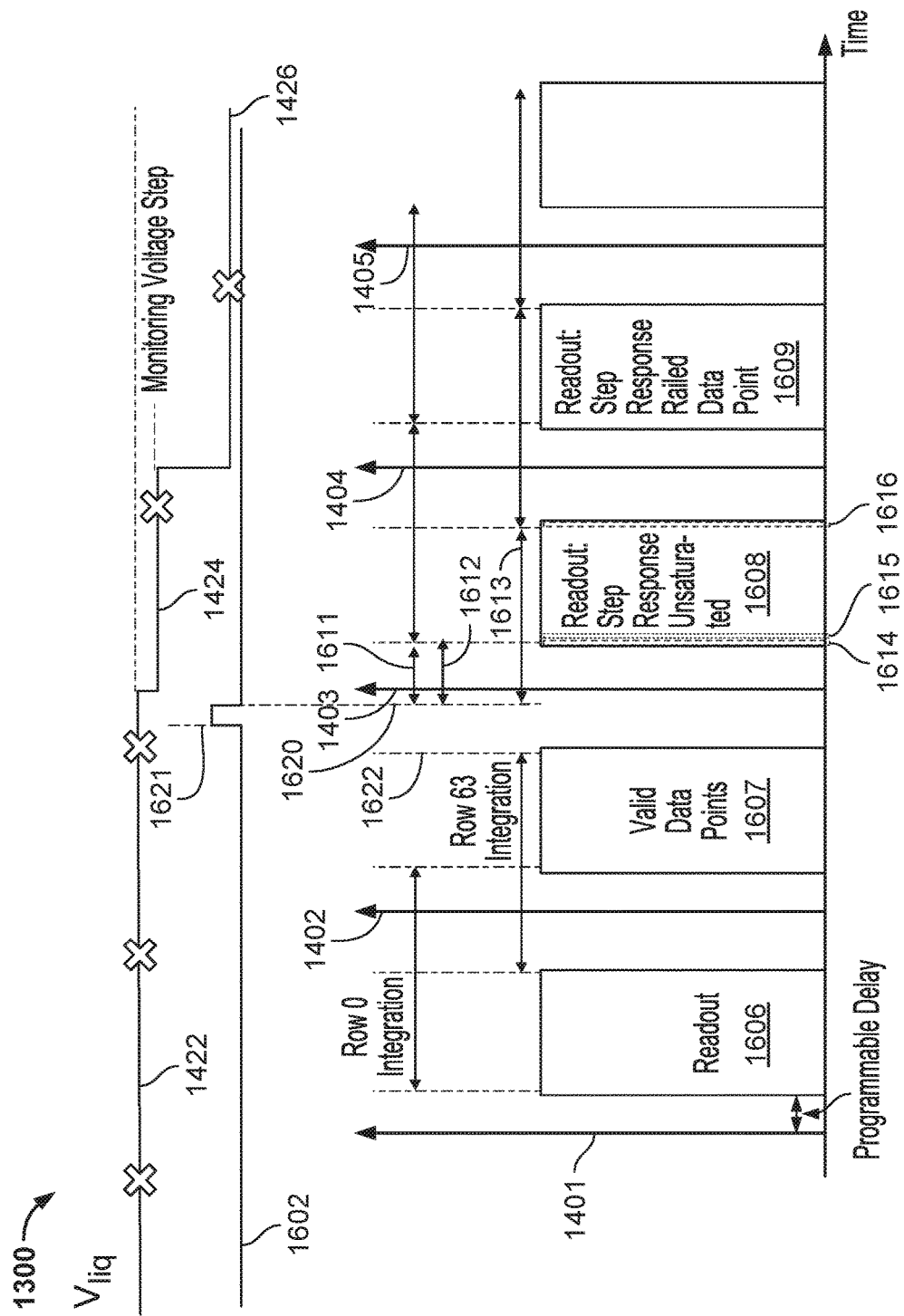
FIG. 16 illustrates that a modified global pre-charge signal 1602 is used to synchronize the integration of the cells in different rows of the cell bank when $V_{liq}$ is about to switch to the intermediate monitoring signal.

FIG. 16 illustrates that a modified global pre-charge signal 1602 is used to synchronize the integration of the cells in different rows of the cell bank when $V_{liq}$ is about to switch to the intermediate monitoring signal. FIG. 15 and FIG. 16 are similar apart from a few differences: one difference is the modification of the global pre-charge signal 1602, as will be described in greater detail below; another difference is that in FIG. 16, the data points 1607 that are useful for sequencing purposes are no longer corrupted by the global pre-charge signal 1602.

Global pre-charge signal 1602 is a pre-charge signal that is used to control switch 601 across all of the cells in a cell bank. In contrast, reset signal 603 is a pre-charge signal that is used to control switch 601 in a single cell or only cells in a single row of the cell bank. As shown in FIG. 16, global pre-charge signal 1602 is set to high at time 1621, which closes all the switches 601 in the cells of the cell bank such that all the integrating capacitors 608 are connected to voltage source $V_{pre}$ 605 and pre-charged to the $V_{pre}$ voltage level. Global pre-charge signal 1602 is then set to low at time 1620, which opens all the switches 601 in the cells of the cell bank such that all integrating capacitors 608 are disconnected from voltage source $V_{pre}$ 605 and start to discharge and integrate at the same time (see integration time intervals 1611, 1612, and 1613).

After the integration time interval 1611 for row 0 is over, the voltage stored in integrating capacitor 608 of each of the cells in row 0 may be read out by ADC 610 at time 1614. After row 0 is read, the integration time interval 1612 for row 1 is over, and the voltage stored in integrating capacitor 608 of each of the cells in row 1 may be read out by ADC 610 at time 1615. Similarly, the subsequent rows are read out one by one, until row 63 is read out at time 1616.

Although the length of the integration time intervals for different rows are not identical (for example, the lengths of 1611, 1612, and 1613 are different), when $V_{liq}$ 1300 is at intermediate monitoring signal magnitude 1424, all of the cells—irrespective of which row they belong to—integrate while the $V_{liq}$ magnitude is maintained at intermediate monitoring signal magnitude 1424. As a result, the ADC outputs in different rows have less variance, thereby reducing the row dependence effect.

In addition, the data points 1607 that are useful for sequencing purposes are no longer corrupted by global pre-charge signal 1602. Global pre-charge signal 1602 is set to high at time 1621, which occurs after time 1622, the time when the readout during frame 1402 (the frame that is prior to the monitoring voltage step) has been completed, thereby preserving the data points 1607 that are useful for sequencing purposes. Global pre-charge signal 1602 is then set to low at time 1620. In some embodiments, time 1620 is at the same time as frame 1403, the frame when $V_{liq}$ 1300 is switched to intermediate monitoring magnitude 1424. In some embodiments, time 1620 is substantially at the same time as frame 1403, either immediately prior to frame 1403 or immediately after frame 1403.

FIG. 17A illustrates the row dependence effect of the lipid membrane state detection technique. In FIG. 17A, the bottom portion is a plot of the observed voltage change $\Delta V_{ADC}$ in response to the monitoring signal in cells that belong to different rows of a cell bank when ruptured lipid bilayers are detected. On the x-axis, row numbers 0-63 corresponds to row numbers 0-63 in cell bank 1, row numbers 64-127 corresponds to row numbers 0-63 in cell bank 2, row numbers 128-191 corresponds to row numbers 0-63 in cell bank 3, and row numbers 192-255 corresponds to row numbers 0-63 in cell bank 4. On the y-axis, the responses to the monitoring signal are plotted in ADC counts. As shown in the bottom portion of FIG. 17A, the response signals gradually increase as the row number increases. The majority of the response signals range from around 15 to 40 ADC counts. The top portion of FIG. 17A is a histogram that shows the distribution of the response signals. The response signals range from 0 to about 40 ADC counts.

FIG. 17B illustrates that the row dependence effect is significantly reduced by using the global pre-charge signal in FIG. 16. In FIG. 17B, the bottom portion is a plot of the observed voltage change $\Delta V_{ADC}$ in response to the monitoring signal in cells that belong to different rows of a cell bank when ruptured lipid bilayers are detected. On the x-axis, row numbers 0-63 corresponds to row numbers 0-63 in cell bank 1, row numbers 64-127 corresponds to row numbers 0-63 in cell bank 2, row numbers 128-191 corresponds to row numbers 0-63 in cell bank 3, and row numbers 192-255 corresponds to row numbers 0-63 in cell bank 4. On the y-axis, the responses to the monitoring signal are plotted in ADC counts. As shown in the bottom portion of FIG. 17B, the response signals increase only slightly as the row number increases. The majority of the response signals range from around 40 to 60 ADC counts. The top portion of FIG. 17B is a histogram that shows the distribution of the response signals. The response signals range from 40 to about 60 ADC counts, with approximately 50 ADC counts being the most likely ADC value.

FIG. 18A is a plot of the observed voltage change $\Delta V_{ADC}$ in response to the monitoring signal in cells that belong to different rows of a cell bank when ruptured lipid bilayers are detected. FIG. 18B is a histogram that shows the distribution of the response signals when ruptured lipid bilayers are detected. FIG. 18C is a plot of the observed voltage change $\Delta V_{ADC}$ in response to the monitoring signal in cells that belong to different rows of a cell bank when ruptured lipid bilayers are not detected. FIG. 18D is a histogram that shows the distribution of the response signals when ruptured lipid bilayers are not detected.

As shown in FIG. 18D, the response signals range from 0 to about 45 ADC counts when ruptured lipid bilayers are not detected; and as shown in FIG. 18B, the response signals range from about 55 to 120 ADC counts when ruptured lipid bilayers are detected. Since the response signals range for the two lipid bilayer conditions do not overlap with each other, the detection technique may be used to reliably determine whether a lipid bilayer is intact or ruptured.

The above disclosed detection technique has many advantages. The selection of the monitoring signal magnitude is decoupled from the selection of the $V_{liq}$ bright/dark magnitudes. The ADC reference window may be selected to increase the resolution of the signals used for nucleic acid sequencing, without causing the response signals to the monitoring signal to saturate. The technique may be used to detect the condition of bilayers even during the sequencing stage. In addition, the technique may reliably detect the condition of bilayers when the modulation frequency of $V_{liq}$ is beyond 100 Hz.

As described above, when the lipid solvent mixture is first deposited into the cells to form the lipid bilayers, some of the cells have lipid bilayers spontaneously formed, but some of the cells merely have a thick lipid membrane with multiple layers of lipid molecules combined with the solvent spanning across each of the wells of the cells. In order to increase the yield of the nanopore based sequencing chip (i.e., the percentage of cells in the nanopore based sequencing chip with properly formed lipid bilayers and nanopores), the nanopore based sequencing chip may perform additional steps to facilitate the formation of lipid bilayers in additional cells. For example, applying an electrical lipid-thinning stimulus to the cells that have not had lipid bilayers formed therein yet can improve the efficiency of liquid flow above the thick lipid membranes, thereby facilitating the removal of any excess lipid solvent such that the thick lipid membranes can be thinned out and transitioned into lipid bilayers more efficiently. Applying the electrical lipid-thinning stimulus to the cells that have not had lipid bilayers formed therein yet will also create electrostatic forces that tend to squeeze out the excess lipid solvent and thin out the thick lipid membranes into lipid bilayers. On the other hand, the cells that have already had lipid bilayers properly formed therein should not be further exposed to the same electrical lipid-thinning stimulus, as the electrical stimulus may cause some of the thin lipid bilayers to break down. Therefore, it is advantageous to use the non-destructive technique described in the present application to detect and separate the portion of the cells in the nanopore based sequencing chip that have lipid bilayers formed therein from the portion of the cells that do not have lipid bilayer properly formed therein yet. By dividing the cells into different groups, the cells in different groups can be processed differently, thereby achieving greater efficiency and increasing the overall yield of the nanopore based sequencing chip.

Figure 19:
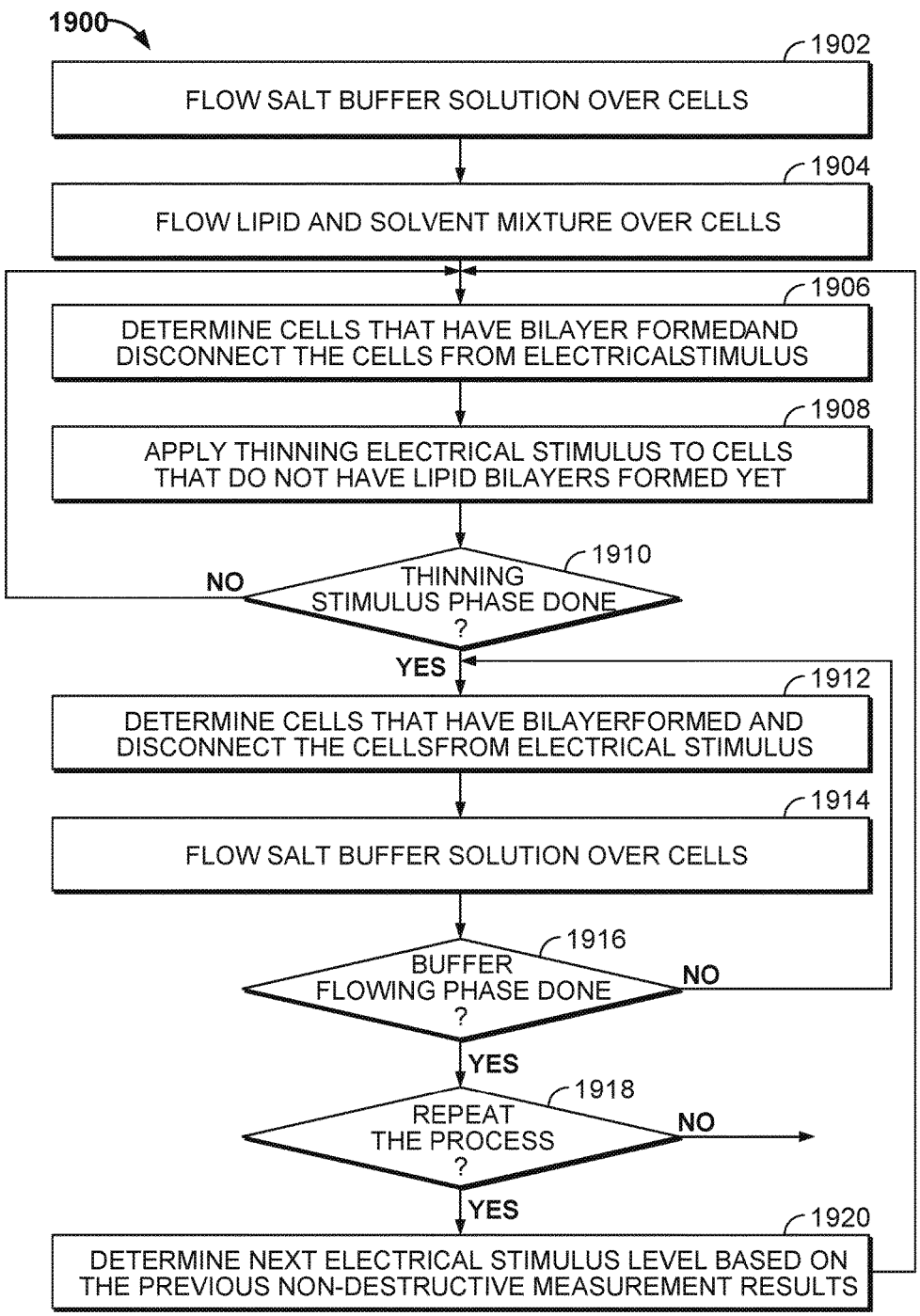
FIG. 19 illustrates an embodiment of a process 1900 for an improved technique of forming lipid layers in the cells of a nanopore based sequencing chip.

FIG. 19 illustrates an embodiment of a process 1900 for an improved technique of forming lipid layers in the cells of a nanopore based sequencing chip. In some embodiments, the nanopore based sequencing chip of FIG. 19 includes a plurality of cells 100 of FIG. 1. In some embodiments, the nanopore based sequencing chip of FIG. 19 includes a plurality of cells 500 of FIG. 5. In some embodiments, the nanopore based sequencing chip of FIG. 19 includes circuitries 600 of FIGS. 6A and 6B.

Process 1900 includes steps in which different types of fluids (e.g., liquids or gases) are flowed through the cells of the nanopore based sequencing chip via a flow chamber. Multiple fluids with significantly different properties (e.g., compressibility, hydrophobicity, and viscosity) are flowed over an array of sensors on the surface of the nanopore based sequencing chip. For improved efficiency, each of the sensors in the array should be exposed to the fluids in a consistent manner. For example, each of the different types of fluids should be flowed over the nanopore based sequencing chip such that the fluid may be delivered to the chip, evenly coating and contacting each of the cells' surfaces, and then delivered out of the chip. As described above, a nanopore based sequencing chip incorporates a large number of sensor cells configured as an array. As the nanopore based sequencing chip is scaled to include more and more cells, achieving an even flow of the different types of fluids across the cells of the chip becomes more challenging.

Figure 20:
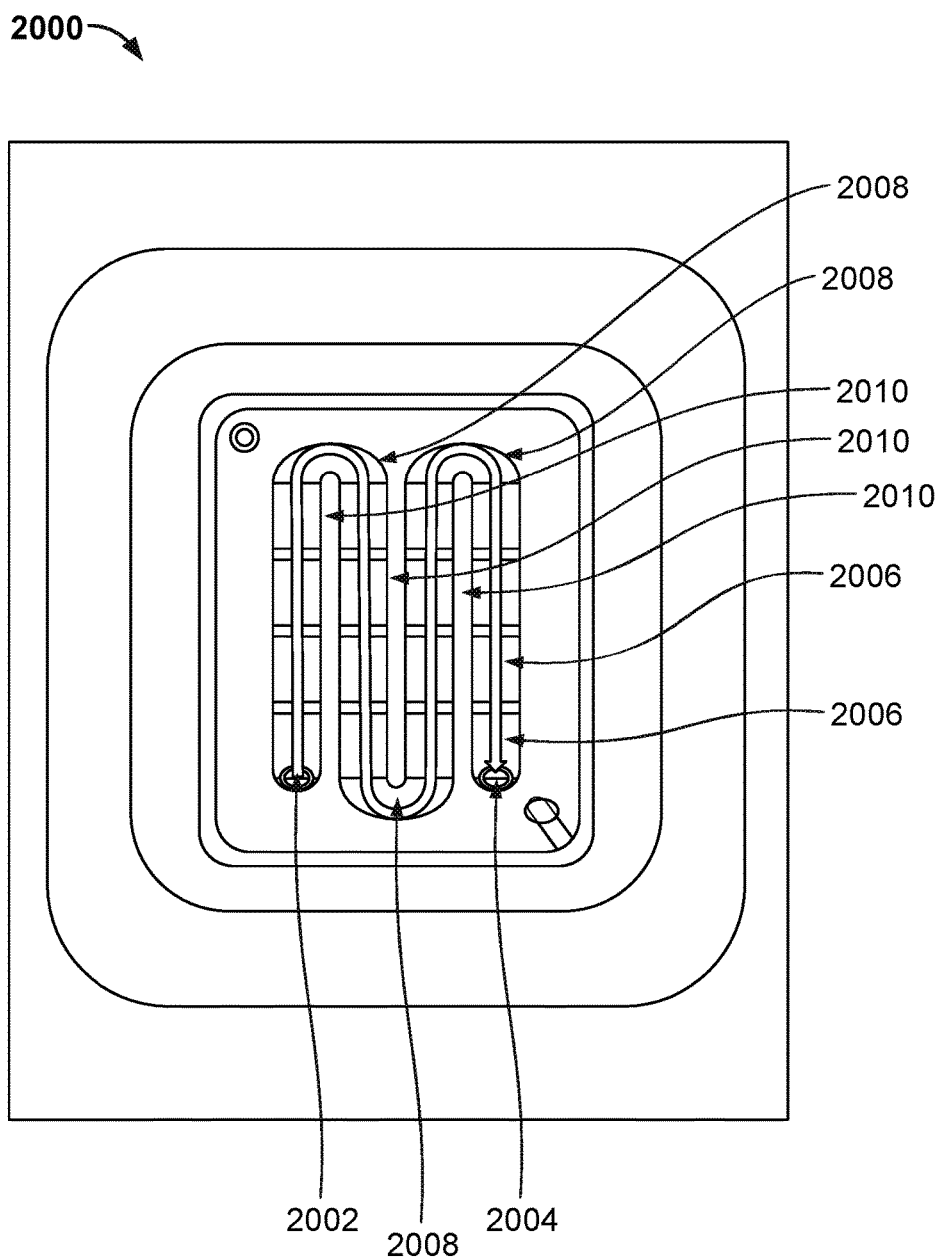
FIG. 20 illustrates the top view of a nanopore based sequencing system 2000 with an improved flow chamber enclosing a silicon chip that allows liquids and gases to pass over and contact sensors on the chip surface.

In some embodiments, the nanopore based sequencing system that performs process 1900 of FIG. 19 includes an improved flow chamber having a serpentine fluid flow channel that directs the fluids to traverse over different sensors of the chip along the length of the channel. FIG. 20 illustrates the top view of a nanopore based sequencing system 2000 with an improved flow chamber enclosing a silicon chip that allows liquids and gases to pass over and contact sensors on the chip surface. The flow chamber includes a serpentine or winding flow channel 2008 that directs the fluids to flow directly above a single column (or a single row) of sensor banks 2006 (each bank including several thousands of sensor cells) from one end of the chip to the opposite end and then directs the fluids to repeatedly loop back and flow directly above other adjacent columns of sensor banks, until all of the sensor banks have been traversed at least once. As shown in FIG. 20, system 2000 includes an inlet 2002 and an outlet 2004.

With reference to FIG. 20, a fluid is directed into system 2000 through inlet 2002. Inlet 2002 may be a tube or a needle. For example, the tube or needle may have a diameter of one millimeter. Instead of feeding the liquid or gas directly into a wide flow chamber with a single continuous space, inlet 2002 feeds the liquid or gas into a serpentine flow channel 2008 that directs the liquid or gas to flow directly above a single column of sensor banks 2006. The serpentine channel 2008 may be formed by stacking together a top plate and a gasket with dividers 2010 that divide the chamber into the serpentine channel to form a flow cell, and then mounting the flow cell on top of the chip. Once the liquid or gas flows through the serpentine channel 2008, the liquid or gas is directed up through outlet 2004 and out of system 2000.

System 2000 allows the fluids to flow more evenly on top of all the sensors on the chip surface. The channel width is configured to be narrow enough such that capillary action has an effect. More particularly, the surface tension (which is caused by cohesion within the fluid) and adhesive forces between the fluid and the enclosing surfaces act to hold the fluid together, thereby preventing the fluid or the air bubbles from breaking up and creating dead zones. For example, the channel may have a width of 1 millimeter or less. The narrow channel enables controlled flow of the fluids and minimizes the amount of remnants from a previous flow of fluids or gases.

With reference to FIG. 19, at 1902, a salt/electrolyte buffer solution is flowed through the cells of the nanopore based sequencing chip via the flow chamber to substantially fill the wells in the cells with the salt buffer solution. The salt buffer solution may include one of the following: lithium chloride (LiCl), sodelectium chloride (NaCl), potassium chloride (KCl), lithium glutamate, sodium glutamate, potassium glutamate, lithium acetate, sodium acetate, potassium acetate, calcium chloride ($CaCl_2$), strontium chloride ($SrCl_2$), Manganese chloride ($MnCl_2$), and magnesium chloride ($MgCl_2$). In some embodiments, the concentration of the salt buffer solution is 300 mM (millimolar).

At 1904, a lipid and solvent mixture is flowed through the cells of the nanopore based sequencing chip via the flow chamber. In some embodiments, the lipid and solvent mixture includes lipid molecules such as diphytanoylphosphatidylcholine (DPhPC). In some embodiments, the lipid and solvent mixture includes decane or tridecane. When the lipid and solvent mixture is first deposited into the cells to form the lipid bilayers, some of the cells have lipid bilayers spontaneously formed, but some of the cells merely have a thick lipid membrane (with multiple layers of lipid molecules and solvent combined together) spanning across each of the wells of the cells. In order to increase the yield of the nanopore based sequencing chip (i.e., the percentage of cells in the nanopore based sequencing chip with properly formed lipid bilayers and nanopores), the nanopore based sequencing chip will repeatedly go through two phases, an electrical lipid-thinning stimulus phase and a buffer flowing phase, to facilitate the formation of lipid bilayers in additional cells.

The electrical lipid-thinning stimulus phase of process 1900 includes steps 1906, 1908, and 1910. In some embodiments, during this phase steps 1906, 1908, and 1910 may be performed in the order as shown in FIG. 19. In some embodiments, steps 1906, 1908, and 1910 may be performed in a different order. In some embodiments, the steps may be performed simultaneously.

At 1906, the non-destructive technique described in the present application is used to detect whether a lipid bilayer is formed in a cell using circuitry 600 of FIG. 6A and FIG. 6B. The detection includes monitoring a voltage change, $\Delta V_{ADC}$, at integrating capacitor 608 ($n_{cap}$) in response to a voltage change ($\Delta V_{liq}$) applied to the bulk liquid in contact with the lipid membrane/bilayer. Cells that have lipid bilayers detected are separated into a different group from the cells that do not have lipid bilayers detected. Within each of the cells with lipid bilayers detected, pass device 606 is opened in order to disconnect the lipid bilayer and the electrodes from the measurement circuitry 600, such that the electrical lipid-thinning stimulus is disabled from being applied to the cell.

At 1908, an electrical lipid-thinning stimulus is applied to the cells of the nanopore based sequencing chip. Applying the electrical lipid-thinning stimulus to the cells that have not had lipid bilayers formed therein yet can improve the efficiency of liquid flow above the thick lipid membranes, thereby facilitating the removal of any excess lipid solvent such that the thick lipid membranes can be thinned out and transitioned into lipid bilayers more efficiently. Applying the electrical lipid-thinning stimulus to the cells that have not had lipid bilayers formed therein yet will also create electrostatic forces that tend to squeeze out the excess lipid solvent and thin out the thick lipid membranes into lipid bilayers. In some embodiments, the same circuitry 600 of FIG. 6A and FIG. 6B may be used to apply the electrical lipid-thinning stimulus. The only difference in the setup of circuitry 600 between lipid bilayer detection and lipid thinning is that the absolute magnitude of $V_{liq}$ is lower for lipid bilayer detection. For example, the absolute magnitude $V_{liq}$ for lipid bilayer detection may be between 100 mV to 250 mV, while the absolute magnitude $V_{liq}$ for lipid thinning may be between 250 mV to 500 mV.

At step 1910, it is determined whether the electrical lipid-thinning stimulus phase is finished. In some embodiments, the electrical lipid-thinning stimulus is applied to any cells that have not been detected as having lipid bilayers therein for a period of two seconds. However, other predetermined period of time may be used as well. If the phase is not over yet, then process 1900 returns to steps 1906 and 1908 again until the time period is finished; otherwise, process 1900 proceeds to the salt buffer solution flowing phase next.

The salt buffer solution flowing phase of process 1900 includes steps 1912, 1914, and 1916. In some embodiments, during this phase steps 1912, 1914, and 1916 may be performed in the order as shown in FIG. 19. In some embodiments, steps 1912, 1914, and 1916 may be performed in a different order. In some embodiments, the steps may be performed simultaneously.

At 1912, the same non-destructive technique used at step 1906 is used to detect whether a lipid bilayer is formed in the cell using circuitry 600 of FIG. 6A and FIG. 6B. Cells that have lipid bilayers detected are separated into a different group from the cells that do not have lipid bilayers detected. Within each of the cells with lipid bilayers detected, pass device 606 is opened in order to disconnect the lipid bilayer and the electrodes from the measurement circuitry 600.

At 1914, a salt/electrolyte buffer solution is flowed through the cells of the nanopore based sequencing chip via the flow chamber. The purpose of flowing the salt buffer solution over the cells is to facilitate the formation of a lipid bilayer over each of the cells. When the salt buffer solution is flowed over the cells, the thickness of the lipid and solvent mixture deposited on the cell is reduced, facilitating the formation of the lipid bilayer.

At 1916, it is determined whether the salt buffer solution flowing phase is over. In some embodiments, salt buffer solution is flowed for a period of two seconds. However, other predetermined period of time may be used as well. If the phase is not over yet, then process 1900 returns to steps 1912 and 1914 again until the time period is finished; otherwise, process 1900 proceeds to step 1918.

At 1918, it is determined whether the electrical lipid-thinning stimulus phase and salt buffer solution flowing phase of process 1900 should be repeated. Different criteria may be used at this step. In some embodiments, the electrical lipid-thinning stimulus phase and salt buffer solution flowing phase are performed a predetermined number of times. In some embodiments, the two phases are repeated until a target yield for the nanopore based sequencing chip has been reached. In some embodiments, if the incremental number or percentage of cells that have just been detected as having lipid bilayers formed during the last round of thinning by the stimulus and the buffer solution flow is lower than a predetermined threshold, then process 1000 is terminated. In some embodiments, the two phases are repeated until the most recently applied electrical lipid-thinning stimulus level has reached a predetermined maximum threshold, e.g. 500 mV.

Process 1900 proceeds to step 1920 if the electrical lipid-thinning stimulus phase and salt buffer solution flowing phase of process 1900 are going to be repeated next. At step 1920, the next electrical lipid-thinning stimulus to be applied is determined. In some embodiments, the electrical lipid-thinning stimulus level is increased by a fixed predetermined amount, e.g., an increment of 100 mV. In some embodiments, if the incremental number or percentage of cells that have just been detected as having lipid bilayers formed during the last iteration is lower than a predetermined threshold, then the electrical lipid-thinning stimulus level is increased by a fixed predetermined amount; otherwise, the previous electrical lipid-thinning stimulus is found to be effective and thus the same electrical lipid-thinning stimulus level is used again.

Figure 21A:
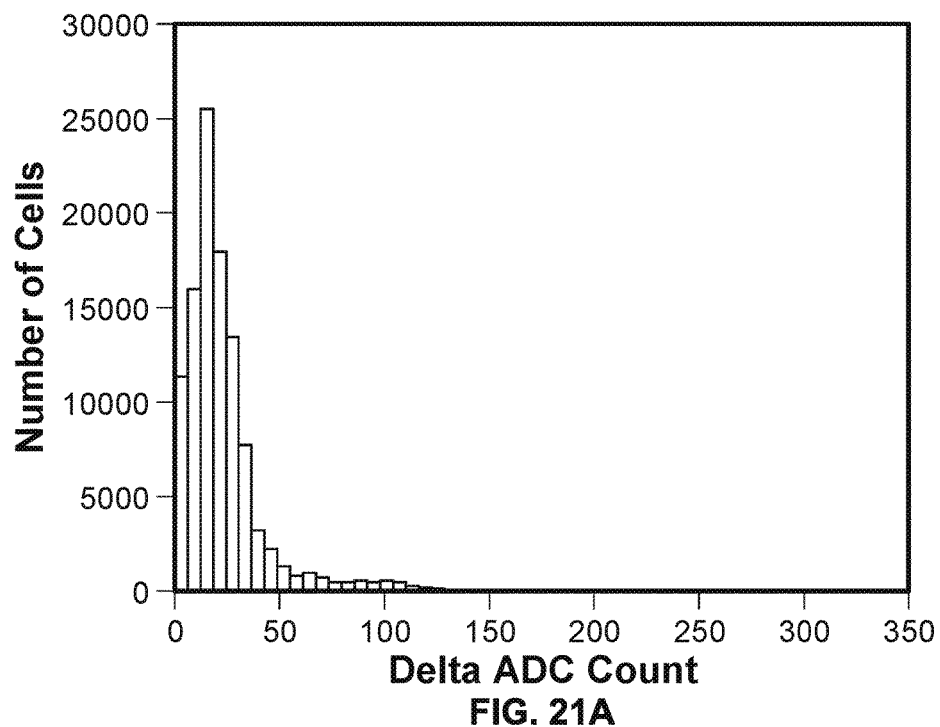
FIG. 21A illustrates the initial distribution of cells with different $\Delta V_{ADC}$ values.
Figure 21B:
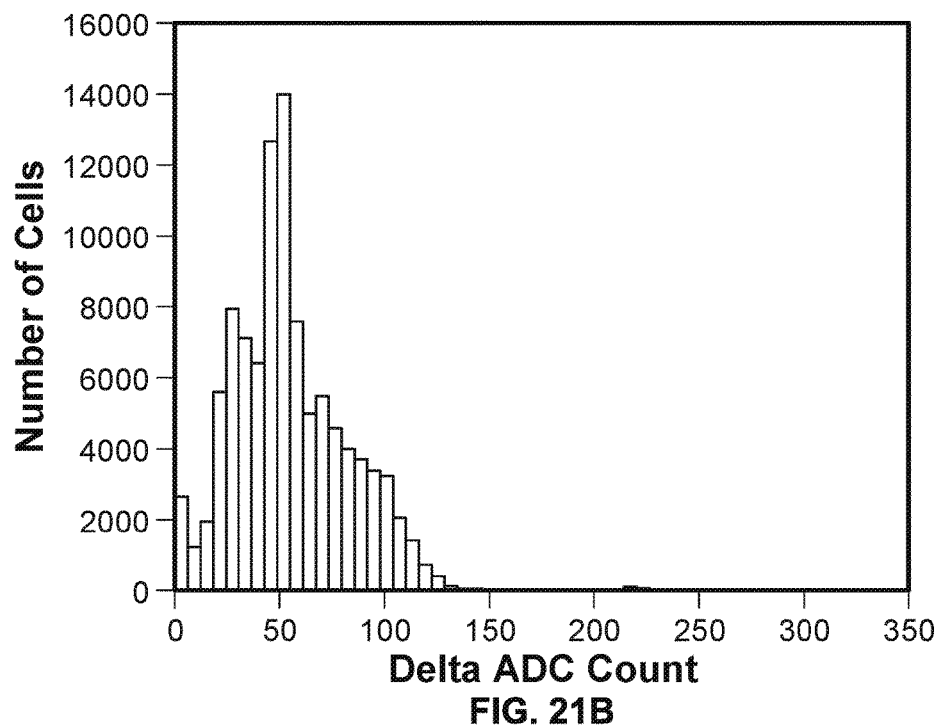
FIG. 21B illustrates the distribution of cells with different $\Delta V_{ADC}$ values after the lipid-thinning stimulus phase and salt buffer solution flowing phase of process 1000 have repeated a number of times.
Figure 21C:
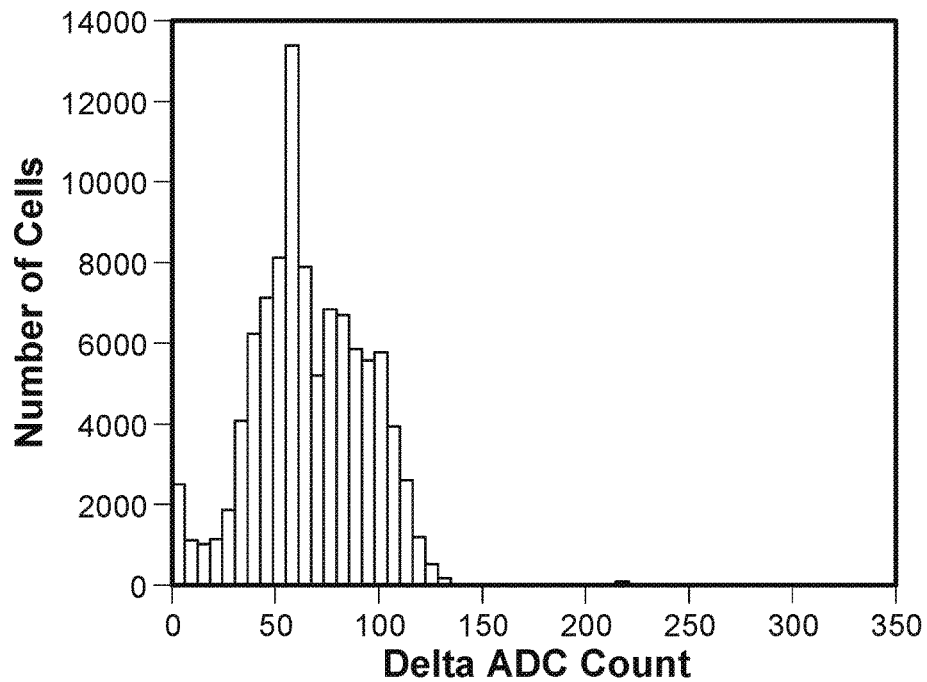
FIG. 21C illustrates the distribution of cells with different $\Delta V_{ADC}$ values after the lipid-thinning stimulus phase and salt buffer solution flowing phase of process 1000 have repeated an even greater number of times.

FIGS. 21A, 21B, and 21C are histograms that illustrate that as the electrical lipid-thinning stimulus phase and salt buffer solution flowing phase of process 1900 repeats a number of times, the overall percentage of cells in the nanopore based sequencing chip with properly formed lipid bilayers (i.e., the yield of the nanopore based sequencing chip) increases. For each of the figures, the x-axis is the voltage change at integrating capacitor 608 ($n_{cap}$), $\Delta V_{ADC}$, in response to a voltage change ($\Delta V_{liq}$) applied to the bulk liquid in contact with the lipid membrane/bilayer, while the y-axis is the number of cells with its $\Delta V_{ADC}$ value within certain $\Delta V_{ADC}$ bins. FIG. 21A illustrates the initial distribution of cells with different $\Delta V_{ADC}$ values. FIG. 21B illustrates the distribution of cells with different $\Delta V_{ADC}$ values after the lipid-thinning stimulus phase and salt buffer solution flowing phase of process 1000 have repeated a number of times. FIG. 21C illustrates the distribution of cells with different $\Delta V_{ADC}$ values after the lipid-thinning stimulus phase and salt buffer solution flowing phase of process 1000 have repeated an even greater number of times. In this example, cells that have a $\Delta V_{ADC}$ value of 50 or above are determined as having lipid bilayers formed therein. As shown in FIG. 21A, initially, only a small number of cells have lipid bilayers detected. As shown in FIG. 21B, after the lipid-thinning stimulus phase and salt buffer solution flowing phase of process 1900 have repeated a number of times, the number of cells having lipid bilayers detected increases. Finally, as shown in FIG. 21C, after the lipid-thinning stimulus phase and salt buffer solution flowing phase of process 1900 have repeated an even greater number of times, a high majority of the cells in the nanopore based sequencing chip has lipid bilayers detected.

Figure 22:
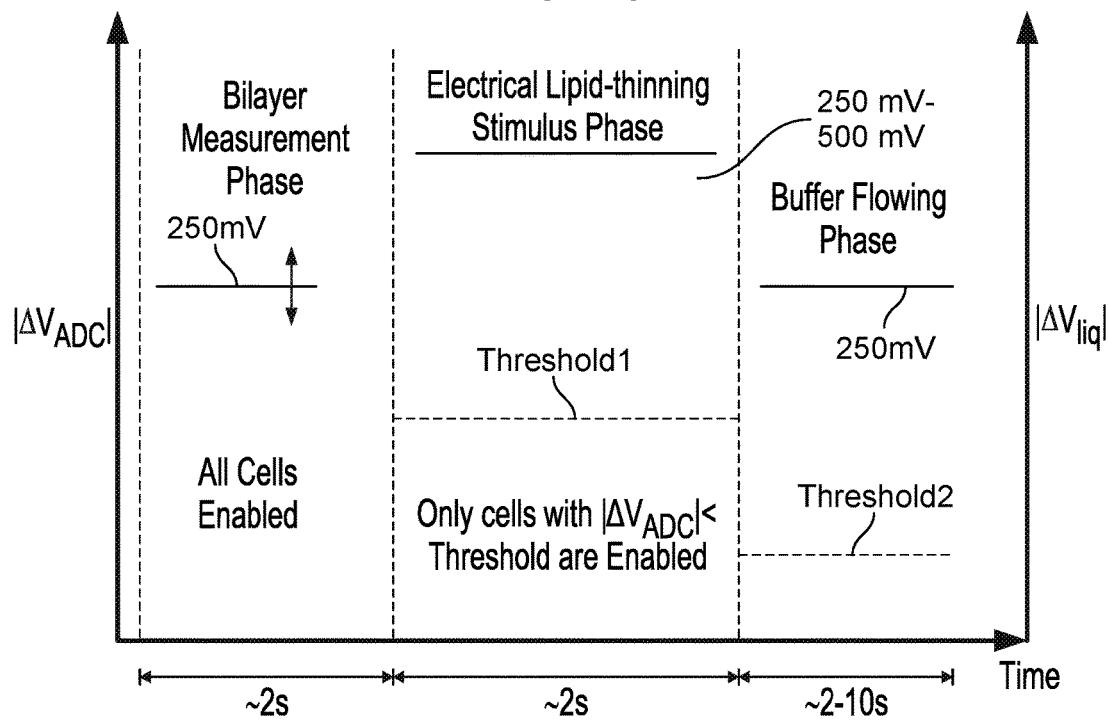
FIG. 22 illustrates an embodiment of a timing diagram for a bilayer measurement phase, an electrical lipid-thinning stimulus phase, and a salt buffer solution flowing phase.

FIG. 22 illustrates an embodiment of a timing diagram for a bilayer measurement phase, an electrical lipid-thinning stimulus phase, and a salt buffer solution flowing phase. In this example, after lipids are deposited into the cells, the bilayer measurement phase is started. The bilayer measurement phase lasts about 2 seconds in time. During this phase, all of the cells are enabled. The absolute value of $V_{liq}$ is 250 mV.

The bilayer measurement phase is followed by the electrical lipid-thinning stimulus phase, which lasts about 2 seconds in time. During this phase, when the absolute value of $\Delta V_{ADC}$ ($|\Delta V_{ADC}|$) exceeds threshold1 within a cell, then a lipid bilayer is detected within the cell and the cell is disconnected from the voltage source. The absolute value of $V_{liq}$ is between 250-500 mV.

The electrical lipid-thinning stimulus phase is followed by the salt buffer solution flowing phase, and the latter lasts about 2-10 seconds in time. During this phase, when the absolute value of $\Delta V_{ADC}$ ($|\Delta V_{ADC}|$) exceeds threshold2 within a cell, then a lipid bilayer is detected within the cell and the cell is disconnected from the voltage source. The absolute value of $V_{liq}$ is 250 mV.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A method of detecting a state of a lipid membrane in a cell of a nanopore based sequencing chip, comprising:
    coupling a lipid membrane with an integrating capacitor, wherein the lipid membrane is between a working electrode and a counter electrode;
    applying an alternating current (AC) voltage to the counter electrode;
    periodically sampling a voltage across the integrating capacitor by an analog-to-digital converter (ADC);
    determining a change in the sampled voltage across the integrating capacitor in response to an intermediate change in the AC voltage, wherein the intermediate change is made when the AC voltage is switching from a first phase to a second phase or when the AC voltage is switching from the second phase to the first phase, wherein a first phase magnitude of the AC voltage is greater than a second phase magnitude of the AC voltage, and wherein the intermediate change comprises a change in the AC voltage from a first phase magnitude to an intermediate monitoring magnitude or a change in the AC voltage from a second phase magnitude to the intermediate monitoring magnitude, and where the intermediate monitoring magnitude is smaller than the first phase magnitude but greater than the second phase magnitude;
    comparing the change in the sampled voltage across the integrating capacitor against one or more predetermined thresholds;
    detecting a state of the lipid membrane based on the determined change in the sampled voltage across the integrating capacitor in response to the intermediate change in the AC voltage, comprising detecting the state of the lipid membrane based on the comparisons against the one or more predetermined thresholds, wherein the state of the lipid membrane is selected from the group consisting of: a lipid membrane with more than two lipid molecule layers, a lipid bilayer, and a ruptured lipid bilayer; and
    selecting the intermediate monitoring magnitude such that the sampled voltage across the integrating capacitor is within an ADC reference window of the ADC in the event that the lipid bilayer has ruptured.

2. The method of claim 1, wherein the intermediate change in the AC voltage is made between two magnitudes of the AC voltage.

3. The method of claim 1, further comprising determining the change in the sampled voltage across the integrating capacitor in response to the intermediate change in the AC voltage when the AC voltage is switching from a first phase to a second phase or when the AC voltage is switching from the second phase to the first phase, and wherein the first phase comprises a positive square wave and the second phase comprises a negative square wave.

4. The method of claim 1, further comprising selecting the intermediate monitoring magnitude based at least in part on the ADC reference window of the ADC.

5. The method of claim 1, wherein the cell is one of a plurality of cells in a nanopore-based sequencing chip, and wherein the method further comprises:
    pre-charging the integrating capacitor by connecting the integrating capacitor to a constant pre-charging voltage source using a global pre-charge signal, wherein the global pre-charge signal is used to control a timing of the pre-charging of integrating capacitors in the plurality of cells;
    after the integrating capacitor is charged to the constant pre-charging voltage source value, disconnecting the pre-charging voltage source from the integrating capacitor using the global pre-charge signal, wherein the global pre-charge signal is used to control a timing of the disconnecting of the pre-charging voltage source from integrating capacitors in the plurality of cells;
    waiting a predetermined period of time for the integrating capacitor to charge or discharge through a capacitance associated with the lipid bilayer; and
    sampling the voltage across the integrating capacitor after the predetermined waiting period.

6. The method of claim 5, wherein the timing of the disconnecting of the pre-charging voltage source from integrating capacitors in the plurality of cells is set such that the timing is substantially the same as a timing when the AC voltage is switched to the intermediate monitoring magnitude.

7. The method of claim 5, wherein the timing of the pre-charging of integrating capacitors in the plurality of cells is set such that the timing is after a frame of sequencing data from the plurality of cells has been read out, and wherein the frame is one frame prior to a frame when the AC voltage is switched to the intermediate monitoring magnitude, and wherein a frame of sequencing data is the sequencing data corresponding to a period when the AC voltage is at a constant magnitude.

8. The method of claim 1, further comprising:
in response to the detection that the lipid bilayer has ruptured, disabling further electrical stimuli from being applied across the lipid bilayer by opening a switch in the cell.

9. A system for detecting a state of a lipid membrane in a cell of a nanopore based sequencing chip, comprising:
an integrating capacitor;
a working electrode coupled to the integrating capacitor;
a counter electrode, wherein a lipid membrane deposited between the working electrode and the counter electrode is coupled with the integrating capacitor;
an alternating current (AC) voltage source that applies an AC voltage to the counter electrode;
an analog-to-digital converter (ADC) periodically sampling a voltage across the integrating capacitor; and
a processor or a circuitry configured to:
determine a change in the sampled voltage across the integrating capacitor in response to an intermediate change in the AC voltage, wherein the intermediate change is made when the AC voltage is switching from a first phase to a second phase or when the AC voltage is switching from the second phase to the first phase, wherein a first phase magnitude of the AC voltage is greater than a second phase magnitude of the AC voltage, and wherein the intermediate change comprises a change in the AC voltage from a first phase magnitude to an intermediate monitoring magnitude or a change in the AC voltage from a second phase magnitude to the intermediate monitoring magnitude, and where the intermediate monitoring magnitude is smaller than the first phase magnitude but greater than the second phase magnitude;
compare the change in the sampled voltage across the integrating capacitor against one or more predetermined thresholds;
detect a state of the lipid membrane based on the determined change in the sampled voltage across the integrating capacitor in response to the intermediate change in the AC voltage, comprising detecting the state of the lipid membrane based on the comparisons against the one or more predetermined thresholds, wherein the state of the lipid membrane is selected from the group consisting of: a lipid membrane with more than two lipid molecule layers, a lipid bilayer, and a ruptured lipid bilayer; and
select the intermediate monitoring magnitude such that the sampled voltage across the integrating capacitor is within an ADC reference window of the ADC in the event that the lipid bilayer has ruptured.

10. The system of claim 9, wherein the intermediate change in the AC voltage is made between two magnitudes of the AC voltage.

11. The system of claim 9, wherein the processor or circuitry is further configured to:
determine the change in the sampled voltage across the integrating capacitor in response to the intermediate change in the AC voltage when the AC voltage is switching from a first phase to a second phase or when the AC voltage is switching from the second phase to the first phase, and wherein the first phase comprises a positive square wave and the second phase comprises a negative square wave.

12. The system of claim 9, wherein the processor or circuitry is further configured to:
select the intermediate monitoring magnitude based at least in part on a ADC reference window of the ADC.

13. The system of claim 9, wherein the cell is one of a plurality of cells in a nanopore-based sequencing chip, further comprising:
a constant pre-charging voltage source;
wherein the processor or circuitry is further configured to:
pre-charge the integrating capacitor by connecting the integrating capacitor to the constant pre-charging voltage source using a global pre-charge signal, wherein the global pre-charge signal is used to control a timing of the pre-charging of integrating capacitors in the plurality of cells;
after the integrating capacitor is charged to the constant pre-charging voltage source value, disconnect the pre-charging voltage source from the integrating capacitor using the global pre-charge signal, wherein the global pre-charge signal is used to control a timing of the disconnecting of the pre-charging voltage source from integrating capacitors in the plurality of cells;
wait a predetermined period of time for the integrating capacitor to charge or discharge through a capacitance associated with the lipid bilayer; and
cause the ADC to sample the voltage across the integrating capacitor after the predetermined waiting period.

14. The system of claim 13, wherein the timing of the disconnecting of the pre-charging voltage source from integrating capacitors in the plurality of cells is set such that the timing is substantially the same as a timing when the AC voltage is switched to the intermediate monitoring magnitude.

15. The system of claim 13, wherein the timing of the pre-charging of integrating capacitors in the plurality of cells is set such that the timing is after a frame of sequencing data from the plurality of cells has been read out, and wherein the frame is one frame prior to a frame when the AC voltage is switched to the intermediate monitoring magnitude, and wherein a frame of sequencing data is the sequencing data corresponding to a period when the AC voltage is at a constant magnitude.

16. The system of claim 9, further comprising:
a switch in the cell controlled by the processor or the circuitry;
wherein the processor or circuitry is further configured to:
in response to the detection that the lipid bilayer has ruptured, disable further electrical stimulus from being applied across the lipid bilayer by opening the switch in the cell.

17. A method of detecting a state of a lipid membrane in a cell of a nanopore based sequencing chip, wherein the cell is one of a plurality of cells in the nanopore-based sequencing chip, comprising:
coupling a lipid membrane with an integrating capacitor, wherein the lipid membrane is between a working electrode and a counter electrode;
applying an alternating current (AC) voltage to the counter electrode;

periodically sampling a voltage across the integrating capacitor by an analog-to-digital converter (ADC), comprising:
- pre-charging the integrating capacitor by connecting the integrating capacitor to a constant pre-charging voltage source using a global pre-charge signal, wherein the global pre-charge signal is used to control a timing of the pre-charging of integrating capacitors in the plurality of cells;
- after the integrating capacitor is charged to the constant pre-charging voltage source value, disconnecting the pre-charging voltage source from the integrating capacitor using the global pre-charge signal, wherein the global pre-charge signal is used to control a timing of the disconnecting of the pre-charging voltage source from integrating capacitors in the plurality of cells;
- waiting a predetermined period of time for the integrating capacitor to charge or discharge through a capacitance associated with the lipid bilayer; and
- sampling the voltage across the integrating capacitor after the predetermined waiting period;

determining a change in the sampled voltage across the integrating capacitor in response to an intermediate change in the AC voltage, wherein the intermediate change is made when the AC voltage is switching from a first phase to a second phase or when the AC voltage is switching from the second phase to the first phase, wherein a first phase magnitude of the AC voltage is greater than a second phase magnitude of the AC voltage, and wherein the intermediate change comprises a change in the AC voltage from a first phase magnitude to an intermediate monitoring magnitude or a change in the AC voltage from a second phase magnitude to the intermediate monitoring magnitude, and where the intermediate monitoring magnitude is smaller than the first phase magnitude but greater than the second phase magnitude; and detecting a state of the lipid membrane based on the determined change in the sampled voltage across the integrating capacitor in response to the intermediate change in the AC voltage.

18. A system for detecting a state of a lipid membrane in a cell of a nanopore based sequencing chip, wherein the cell is one of a plurality of cells in the nanopore based sequencing chip, comprising:
- an integrating capacitor;
- a working electrode coupled to the integrating capacitor;
- a counter electrode, wherein a lipid membrane deposited between the working electrode and the counter electrode is coupled with the integrating capacitor;
- an alternating current (AC) voltage source that applies an AC voltage to the counter electrode;
- an analog-to-digital converter (ADC) periodically sampling a voltage across the integrating capacitor;
- a constant pre-charging voltage source; and
- a processor or a circuitry configured to:
  - periodically sample a voltage across the integrating capacitor by the analog-to-digital converter (ADC), comprising:
    - pre-charge the integrating capacitor by connecting the integrating capacitor to the constant pre-charging voltage source using a global pre-charge signal, wherein the global pre-charge signal is used to control a timing of the pre-charging of integrating capacitors in the plurality of cells;
    - after the integrating capacitor is charged to the constant pre-charging voltage source value, disconnect the pre-charging voltage source from the integrating capacitor using the global pre-charge signal, wherein the global pre-charge signal is used to control a timing of the disconnecting of the pre-charging voltage source from integrating capacitors in the plurality of cells;
    - wait a predetermined period of time for the integrating capacitor to charge or discharge through a capacitance associated with the lipid bilayer; and
    - sample the voltage across the integrating capacitor after the predetermined waiting period;
  - determine a change in the sampled voltage across the integrating capacitor in response to an intermediate change in the AC voltage, wherein the intermediate change is made when the AC voltage is switching from a first phase to a second phase or when the AC voltage is switching from the second phase to the first phase, wherein a first phase magnitude of the AC voltage is greater than a second phase magnitude of the AC voltage, and wherein the intermediate change comprises a change in the AC voltage from a first phase magnitude to an intermediate monitoring magnitude or a change in the AC voltage from a second phase magnitude to the intermediate monitoring magnitude, and where the intermediate monitoring magnitude is smaller than the first phase magnitude but greater than the second phase magnitude; and
  - detect a state of the lipid membrane based on the determined change in the sampled voltage across the integrating capacitor in response to the intermediate change in the AC voltage.

* * * * *